(12) United States Patent
Zablocki et al.

(10) Patent No.: US 6,770,634 B1
(45) Date of Patent: *Aug. 3, 2004

(54) C-PYRAZOLE A2A RECEPTOR AGONISTS

(75) Inventors: Jeff A. Zablocki, Mountain View, CA (US); Elfatih O. Elzein, Freemont, CA (US); Venkata P. Palle, Sunnyvale, CA (US)

(73) Assignee: CV Therapeutics, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/018,758

(22) PCT Filed: Jun. 21, 2000

(86) PCT No.: PCT/US00/17095

§ 371 (c)(1),
(2), (4) Date: Mar. 12, 2002

(87) PCT Pub. No.: WO00/78778

PCT Pub. Date: Dec. 28, 2000

Related U.S. Application Data

(63) Continuation of application No. 09/338,327, filed on Jun. 22, 1999, now Pat. No. 6,214,807.

(51) Int. Cl.⁷ .......................... A01N 43/04; A61K 31/70
(52) U.S. Cl. ..................... 514/46; 514/45; 514/47; 536/27.3; 536/27.6; 536/27.61; 536/27.7
(58) Field of Search ............... 514/45, 46, 47; 536/27.3, 27.61, 27.6, 27.7

(56) References Cited

U.S. PATENT DOCUMENTS

| | | |
|---|---|---|
| 4,956,345 A | 9/1990 | Miyasaka et al. |
| 5,189,027 A | 2/1993 | Miyashita et al. |
| 5,270,304 A | 12/1993 | Kogi et al. |
| 5,459,254 A | 10/1995 | Yamaguchi et al. |
| 5,593,975 A | 1/1997 | Cristalli |
| 5,705,491 A | 1/1998 | Yamada |
| 5,770,716 A | 6/1998 | Khan et al. |
| 5,939,543 A | 8/1999 | Morozumi et al. |
| 6,026,317 A | 2/2000 | Verani |
| 6,214,807 B1 * | 4/2001 | Zablocki et al. .............. 514/46 |

FOREIGN PATENT DOCUMENTS

| | | |
|---|---|---|
| CA | 965411 | 4/1975 |
| EP | 0 354 638 | 2/1990 |
| JP | Hei 5[1993]-9197 | 1/1993 |

OTHER PUBLICATIONS

Marumoto, et al., "Synthesis and Coronary Vadodilating Activity of 2–Substituted Adenosines", *Chem.. Pharm. Bull.* 23(4): 759–774 (1975).

Marumoto, et al., "Synthesis and Enzymatic Activity of Adenosine 3',5'–Cyclic Phosphate Analogs", *Chem.. Pharm. Bull.* 27(4) 990–1003 (1979).

Persson, et al., "Synthesis and Antiviral Effects of 2–Heteroaryl Substituted Adenosine and 8–Heteroaryl Substituted Guanosine Derivatives", *Bioorganic & Medicinal Chemistry*, 3:1377–1382 (1995).

Mager, et al., "Molecular simulation applied to 2–(N'alkylidenehydrazino)— and 2–(N'–aralkylidenehydrazino) adenosine $A_2$ Agonists", *Eur. J. Med. Chem,* 30:15–25 (1995).

Cristalli et al., "2–Alkynl Derivatives of Adenosine 5'–N'ethyluronamide: Selective $A_2$ Adenosine Receptor Agonists with Potent Inhibitory Activity on Platelet Aggregation", *J. Med. Chem,* 37:1720–1726 (1994).

Matsuda, et al., "Nucleosides and Nucleotides. 103. 2–Alkynyladenoines: A Novel Class of Selective Adenosine $A_2$ Receptor Agonists with Potent Antihypertensive Effects", *J. Med. Chem.* 35:241–252 (1992).

* cited by examiner

*Primary Examiner*—James O. Wilson
*Assistant Examiner*—Patrick Lewis
(74) *Attorney, Agent, or Firm*—McDonnell Boehnen Hulbert & Berghoff

(57) ABSTRACT

2-adenosine C-pyrazole compounds having formula (a) and methods for using the compounds as A2A receptor agonists to stimulate mammalian coronary vasodilatation for therapeutic purposes and for purposes of imaging the heart.

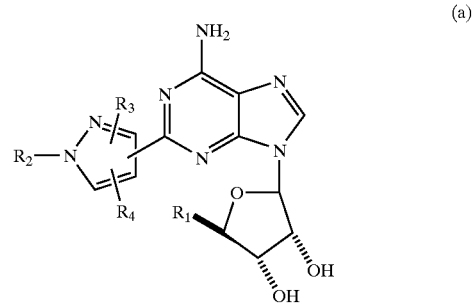

(a)

6 Claims, 3 Drawing Sheets

C-PYRAZOLE A2A RECEPTOR AGONISTS

REFERENCE TO RELATED APPLICATIONS

This application is a 35 U.S.C. §371 filing of PCT Patent Application Serial No. PCT/US00/17095, filed Jun. 21, 2000, which is a con of U.S. patent application Ser. No. 09/338,327, filed Jun. 22, 1999, now U.S. Pat. No. 6,214,807, issued Apr. 10, 2001, all of which are incorporated herein, in their entireties.

BACKGROUND OF THE INVENTION

1. Field of Invention

This invention includes C-pyrazole compounds that are useful as $A_{2A}$ receptor agonists. The compounds of this invention are vasodialating agents that are useful in heart imaging to aid in the identification of mammals, and especially humans who are suffering from disorders such poor coronary perfusion which is indicative of coronary artery disease (CAD). The compounds of this invention can also be used as therapeutics for coronary artery disease.

2. Description of the Art

Pharmacological stress is frequently induced with adenosine or dipyridamole in patients with suspected CAD before imaging with Tl scintigraphy or echocardiography. Both drugs effect dilation of the coronary resistance vessels by activation of cell surface $A_2$ receptors. Although pharmacological stress was originally introduced as a mean of provoking coronary dilation in patients unable to exercise, several studies have shown that the prognostic value of $^{201}Tl$ or echocardiographic imaging in patients subjected to pharmacological stress with adenosine or dipyridamole was equivalent to patients subjected to traditional exercise stress tests. However, there is a high incidence of drug-related adverse side effects during pharmacological stress imaging with these drugs such as headache and nausea, that could be improved with new therapeutic agents.

Adenosine $A_{2B}$ and $A_3$ receptors are involved in a mast cell degranulation and, therefore, asthmatics are not give the non-specific adenosine agonists to induce a pharmacological stress test. Additionally, adenosine stimulation of the $A_1$ receptor in the atrium and A-V node will diminish the S-H interval which can induce AV block. (N. C. Gupto et al.; *J. Am Coll. Cardiol;* (1992) 19: 248–257). Also, stimulation of the adenosine $A_1$ receptor by adenosine may be responsible for the nausea since the $A_1$ receptor is found in the intestinal tract. (J. Nicholls et al.; *Eur. J. Pharm.*(1997) 338(2) 143–150).

Animal data suggests that specific adenosine $A_{2A}$ subtype receptors on coronary resistance vessels mediate the coronary dilatory responses to adenosine, whereas subtype $A_{2B}$ receptor stimulation relaxes peripheral vessels (note: the latter lowers systemic blood pressure). As a result there is a need for pharmaceutical compositions that are $A_{2A}$ receptor agonists that have no pharmacological effect as a result of stimulating the $A_1$ receptor in vivo. Furthermore, there is a need for $A_{2A}$ receptor agonists that have a short half-life, and that are well tolerated by patients undergoing pharmacological coronary stress evaluations.

SUMMARY OF THE INVENTION

In one aspect, this invention includes 2-adenosine C-pyrazole compounds that are useful $A_{2A}$ receptor agonists.

In another aspect, this invention includes pharmaceutical compositions including 2-adenosine C-pyrazole that are well tolerated with few side effects.

Still another aspect of this invention are C-pyrazole compounds that can be easily used in conjunction with radioactive imaging agents to facilitate coronary imaging.

In one embodiment, this invention includes C-pyrazole compounds having the following formula:

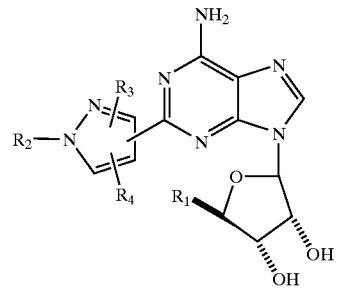

In another embodiment, this invention includes methods for using compounds of this invention to stimulate coronary vasodilatation in mammals, and especially in humans, for stressing the heart to induce a steal situation for purposes of imaging the heart.

In still another embodiment, this invention is a pharmaceutical composition of matter comprising one or more compounds of this invention and one or more pharmaceutical excipients.

DESCRIPTION OF THE CURRENT EMBODIMENT

Figure 1:
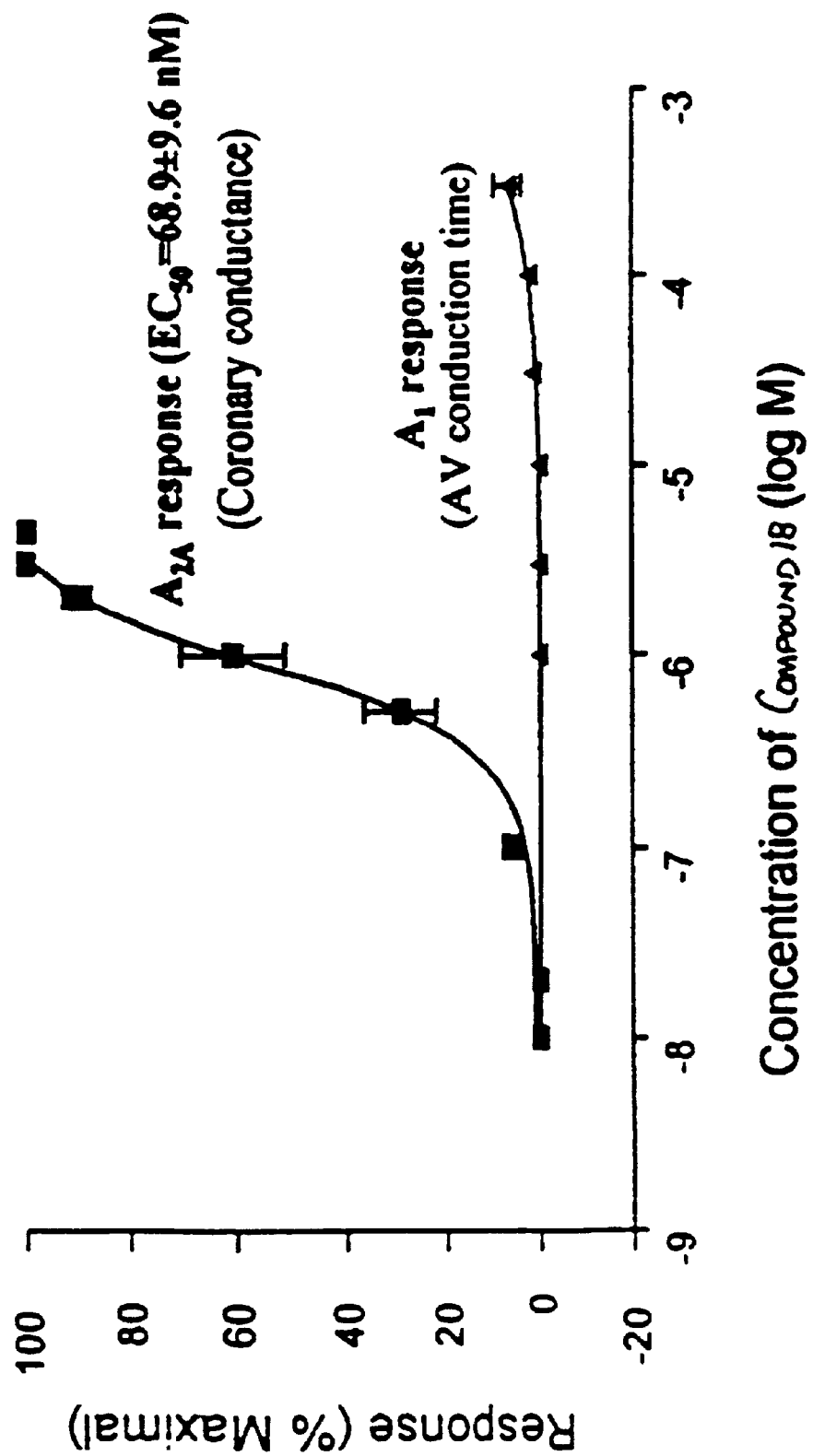
FIG. 1 is a concentration response curve for the $A_1$ adenosine receptor (AdoR)-mediated negative dromotropic (AV conductino time) and $A_{2A}$ AdoR-mediated vasodialator (increase coronary conductance) effects of Compound 18 of this invention in rat isolated perfused hearts. Symbols and error bars indicate means±SEM of single determination from each of four hearts. $EC_{50}$ value (potency) is the concentration of Compound 18 that causes 50% of maximal response.

This compounds of this invention include a class of 2-adenosine C-pyrazole compounds having the following formula:

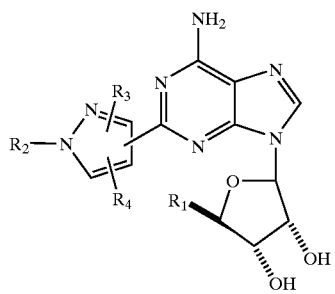

wherein $R^1$ is —CH$_2$OH, and —C(=O)NR$^5$R$^6$;

$R^2$ is selected from the group consisting of hydrogen, C$_{1-15}$ alkyl, C$_{2-15}$ alkenyl, C$_{2-15}$ alkynyl, heterocyclyl, aryl, and heteroaryl, wherein the alkyl, alkenyl, alkynyl, aryl, heterocyclyl, and heteroaryl substituents are optionally substituted with from 1 to 3 substituents independently selected from the group consisting of halo, NO$_2$, heterocyclyl, aryl, heteroaryl, CF$_3$, CN, OR$^{20}$, SR$^{20}$, N(R$^{20}$)$_2$, S(O)R$^{22}$, SO$_2$R$^{22}$, SO$_2$N(R$^{20}$)$_2$, SO$_2$NR$^{20}$COR$^{22}$, SO$_2$NR$^{20}$CO$_2$R$^{22}$, SO$_2$NR$^{20}$CON(R$^{20}$)$_2$, N(R$^{20}$)$_2$ NR$^{20}$COR$^{22}$, NR$^{20}$CO$_2$R$^{22}$, NR$^{20}$CON(R$^{20}$)$_2$, NR$^{20}$C(NR$^{20}$)NHR$^{23}$, COR$^{20}$, CO$_2$R$^{20}$, CON(R$^{20}$)$_2$, CONR$^{20}$SO$_2$R$^{22}$, NR$^{20}$SO$_2$R$^{22}$, SO$_2$NR$^{20}$CO$_2$R$^{22}$, OCONR$^{20}$SO$_2$R$^{22}$, OC(O)R$^{20}$, C(O)OCH$_2$OC(O)R$^{20}$, and OCON(R$^{20}$)$_2$ and wherein each optional heteroaryl, aryl, and heterocyclyl substituent is optionally substituted with halo, NO$_2$, alkyl, CF$_3$, amino, mono- or di- alkylamino, alkyl or aryl or heteroaryl amide, NCOR$^{22}$, NR$^{20}$SO$_2$R$^{22}$, COR$^{20}$, CO$_2$R$^{20}$, CON(R$^{20}$)$_2$, NR$^{20}$CON(R$^{20}$)$_2$, OC(O)R$^{20}$, OC(O)N(R$^{20}$)$_2$, SR$^{20}$, S(O)R$^{22}$, SO$_2$R$^{22}$, SO$_2$N(R$^{20}$)$_2$, CN, or OR$^{20}$;

$R^3$, $R^4$ are individually selected from the group consisting of hydrogen, C$_{1-15}$ alkyl, C$_{2-15}$ alkenyl, C$_{2-15}$ alkynyl, heterocyclyl, aryl, and heteroaryl, halo, NO$_2$, CF$_3$, CN, OR$^{20}$, SR$^{20}$, N(R$^{20}$)$_2$, S(O)R$^{22}$, SO$_2$R$^{22}$, SO$_2$N(R$^{20}$)$_2$, SO$_2$NR$^{20}$COR$^{22}$, SO$_2$NR$^{20}$CO$_2$R$^{22}$, SO$_2$NR$^{20}$CON(R$^{20}$)$_2$, N(R$^{20}$)$_2$ NR$^{20}$COR$^{22}$, NR$^{20}$CO$_2$R$^{22}$, NR$^{20}$CON(R$^{20}$)$_2$, NR$^{20}$C(NR$^{20}$)NHR$^{23}$, COR$^{20}$, CO$_2$R$^{20}$, CON(R$^{20}$)$_2$, CONR$^{20}$SO$_2$R$^{22}$, NR$^{20}$SO$_2$R$^{22}$, SO$_2$NR$^{20}$CO$_2$R$^{22}$, OCONR$^{20}$SO$_2$R$^{22}$, OC(O)R$^{20}$, C(O)OCH$_2$OC(O)R$^{20}$, and OCON(R$^{20}$)$_2$ wherein the alkyl, alkenyl, alkynyl, aryl, heterocyclyl, and heteroaryl substituents are optionally substituted with from 1 to 3 substituents individually selected from the group consisting of halo, NO$_2$, heterocyclyl, aryl, heteroaryl, CF$_3$, CN, OR$^{20}$, SR$^{20}$, N(R$^{20}$)$_2$, S(O)R$^{22}$, SO$_2$R$^{22}$, SO$_2$N(R$^{20}$)$_2$, SO$_2$NR$^{20}$COR$^{22}$, SO$_2$NR$^{20}$CO$_2$R$^{22}$, SO$_2$NR$^{20}$CON(R$^{20}$)$_2$, N(R$^{20}$)$_2$ NR$^{20}$COR$^{22}$, NR$^{20}$CO$_2$R$^{22}$, NR$^{20}$CON(R$^{20}$)$_2$, NR$^{20}$C(NR$^{20}$)NHR$^{23}$, COR$^{20}$, CO$_2$R$^{20}$, CON(R$^{20}$)$_2$, CONR$^{20}$SO$_2$R$^{22}$, NR$^{20}$SO$_2$R$^{22}$, SO$_2$NR$^{20}$CO$_2$R$^{22}$, OCONR$^{20}$SO$_2$R$^{22}$, OC(O)R$^{20}$, C(O)OCH$_2$OC(O)R$^{20}$, and OCON(R$^{20}$)$_2$ and wherein each optional heteroaryl, aryl, and heterocyclyl substituent is optionally substituted with halo, NO$_2$, alkyl, CF$_3$, ammo, mono- or di- alkylamino, alkyl or aryl or heteroaryl amide, NCOR$^{22}$, NR$^{20}$SO$_2$R$^{22}$, COR$^{20}$, CO$_2$R$^{20}$, CON(R$^{20}$)$_2$, NR$^{20}$CON(R$^{20}$)$_2$, OC(O)R$^{20}$, OC(O)N(R$^{20}$)$_2$, SR$^{20}$, S(O)R$^{22}$, SO$_2$R$^{22}$, SO$_2$N(R$^{20}$)$_2$, CN, or OR$^{20}$;

$R^5$ and $R^6$ are each individually H, C1–15 alkyl with from 1 to 2 substituents independently selected from the group consisting of halo, NO$_2$, heterocyclyl, aryl, heteroaryl, CF$_3$, CN, OR$^{20}$, SR$^{20}$, N(R$^{20}$)$_2$, S(O)R$^{22}$, SO$_2$R$^{22}$, SO$_2$N(R$^{20}$)$_2$, SO$_2$NR$^{20}$COR$^{22}$, SO$_2$NR$^{20}$CO$_2$R$^{22}$, SO$_2$NR$^{20}$CON(R$^{20}$)$_2$, N(R$^{20}$)$_2$ NR$^{20}$COR$^{22}$, NR$^{20}$CO$_2$R$^{22}$, NR$^{20}$CON(R$^{20}$)$_2$, NR$^{20}$C(NR$^{20}$)NHR$^{23}$, COR$^{20}$, CO$_2$R$^{20}$, CON(R$^{20}$)$_2$, CONR$^{20}$SO$_2$R$^{22}$, NR$^{20}$SO$_2$R$^{22}$, SO$_2$NR$^{20}$CO$_2$R$^{22}$, OCONR$^{20}$SO$_2$R$^{22}$, OC(O)R$^{20}$, C(O)OCH$_2$OC(O)R$^{20}$, and OCON(R$^{20}$)$_2$ and wherein each optional heteroaryl, aryl, and heterocyclyl substituent is optionally substituted with halo, NO$_2$, alkyl, CF$_3$, amino, mono- or di- alkylamino, alkyl or aryl or heteroaryl amide, NCOR$^{22}$, NR$^{20}$SO$_2$R$^{22}$, COR$^{20}$, CO$_2$R$^{20}$, CON(R$^{20}$)$_2$, NR$^{20}$CON(R$^{20}$)$_2$, OC(O)R$^{20}$, OC(O)N(R$^{20}$)$_2$, SR$^{20}$, S(O)R$^{22}$, SO$_2$R$^{22}$, SO$_2$N(R$^{20}$)$_2$, CN, or OR$^{20}$;

$R^{20}$ is selected from the group consisting of H, C$_{1-15}$ alkyl, C$_{2-15}$ alkenyl, C$_{2-15}$ alkynyl, heterocyclyl, aryl, and heteroaryl, wherein the alkyl, alkenyl, alkynyl, heterocyclyl, aryl, and heteroaryl substituents are optionally substituted with from 1 to 3 substituents independently selected from halo, alkyl, mono- or dialkylamino, alkyl or aryl or heteroaryl amide, CN, O—C$_{1-6}$ alkyl, CF$_3$, aryl, and heteroaryl; and $R^{22}$ is a member selected from the group consisting of C$_{1-15}$ alkyl, C$_{2-15}$ alkenyl, C$_{2-15}$ alkynyl, heterocyclyl, aryl, and heteroaryl, wherein the alkyl, alkenyl, alkynyl, heterocyclyl, aryl, and heteroaryl substituents are optionally substituted with from 1 to 3 substituents independently selected from halo, alkyl, mono- or dialkylamino, alkyl or aryl or heteroaryl amide, CN, O—C$_{1-6}$ alkyl, CF$_3$, and heteroaryl wherein, when $R^1$=CH$_2$OH, $R^3$ is H, $R^4$ is H, the pyrazole ring is attached through C$^4$, and $R^2$ is not H.

When the compound is selected has one of the following formulas:

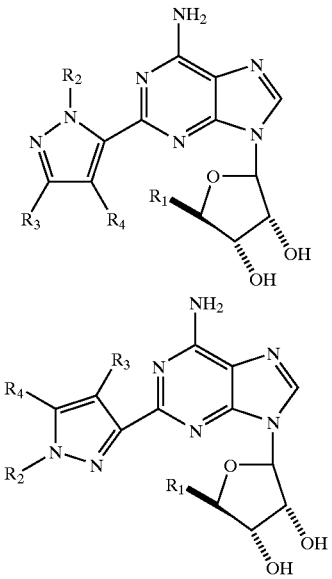

then it is preferred that $R^1$ is —CH$_2$OH; $R^2$ is selected from the group consisting of hydrogen, C$_{1-8}$ alkyl wherein the alkyl is optionally substituted with one substituent independently selected from the group consisting of aryl, CF$_3$, CN, and wherein each optional aryl substituent is optionally substituted with halo, alkyl, CF$_3$ or CN; and $R^3$ and $R^4$ are each independently selected from the group consisting of hydrogen, methyl and more preferably, $R^3$ and $R^4$ are each hydrogen.

When the compound of this invention has the following formulas:

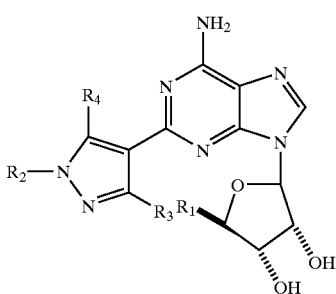

then it is preferred that $R^1$ is —$CH_2OH$; $R^2$ is selected from the group consisting of hydrogen, and $C_{1-6}$ alkyl optionally substituted by phenyl. More preferably, $R^2$ is selected from benzyl and pentyl; $R^3$ is selected from the group consisting of hydrogen, $C_{1-6}$ alkyl, aryl, wherein the alkyl, and aryl substituents are optionally substituted with from 1 to 2 substituents independently selected from the group consisting of halo, aryl, $CF_3$, CN, and wherein each optional aryl substituent is optionally substituted with halo, alkyl, $CF_3$ or CN; and $R^4$ is selected from the group consisting of hydrogen and $C_{1-6}$ alkyl, and more preferably, $R^4$ is selected from hydrogen and methyl.

It is most preferred that the compounds of this invention is selected from (4S,2R,3R,5R)-2-{6-amino-2-[1-benzylpyrazol-4-yl]purin-9-yl}-5-(hydroxymethyl)oxolane-3,4-diol, (4S,2R,3R,5R)-2-[6-amino-2-(1-pentylpyrazol-4-yl)purin-9yl]-5-(hydroxymethyl)oxolane-3,4-diol, (4S,2R,3R,5R)-2-[6-amino-2-(1-methylpyrazol-4-yl)purin-9-yl]-5-(hydroxymethyl)oxolane-3,4-diol, (4S,2R,3R,5R)-2-{6-amino-2-[1-(methylethyl)pyrazol-4-yl]purin-9-yl}-5-(hydroxymethyl)oxolane-3,4-diol, (4S,2R,3R,5R)-2-{6-amino-2-[1-(3-phenylpropyl)pyrazol-4-yl]purin-9-yl}-5-(hydroxymethyl)oxolane-3,4-diol, (4S,2R,3R,5R)-2-{6-amino-2-[1-(4-t-butylbenzyl)pyrazol-4-yl]purin-9-yl}-5-(hydroxymethyl)oxolane-3,4-diol, (4S,2R,3R,5R)-2-(6-amino-2-pyrazol-4-ylpurin-9-yl)-5-(hydroxymethyl)oxolane-3,4-diol, (4S,2R,3R,5R)-2-{6-amino-2-[1-pent-4-enylpyrazol-4-yl]purin-9-yl}-5-(hydroxymethyl)oxolane-3,4-diol, (4S,2R,3R,5R)-2-{6-amino-2-[1-decylpyrazol-4-yl]purin-9-yl}-5-(hydroxymethyl)oxolane-3,4-diol, (4S,2R,3R,5R)-2-{6-amino-2-[1-(cyclohexylmethyl)pyrazol-4-yl]purin-9-yl}-5-(hydroxymethyl)oxolane-3,4-diol, (4S,2R,3R,5R)-2-{6-amino-2-[1-(2-phenylethyl)pyrazol-4yl]purin-9-yl}-5-(hydroxymethyl)oxolane-3,4-diol, (4S,2R,3R,5R)-2-{6-amino-2-[1-(3-cyclohexylpropyl)pyrazol-4-yl]purin-9-yl}-5-(hydroxymethyl)oxolane-3,4-diol, (4S,2R,3R,5R)-2-{6-amino-2-[1-(2-cyclohexylethyl)pyrazol-4-yl]purin-9-yl}-5-(hydroxymethyl)oxolane-3,4-diol, and mixtures thereof.

The following definitions apply to terms as used herein.

"Halo" or "Halogen"—alone or in combination means all halogens, that is, chloro (Cl), fluoro (F), bromo (Br), iodo (I).

"Hydroxyl" refers to the group —OH.

"Thiol" or "mercapto" refers to the group —SH.

"Alkyl"—alone or in combination means an alkane-derived radical containing from 1 to 20, preferably 1 to 15, carbon atoms (unless specifically defined). It is a straight chain alkyl, branched alkyl or cycloalkyl. Preferably, straight or branched alkyl groups containing from 1–15, more preferably 1 to 8, even more preferably 1–6, yet more preferably 1–4 and most preferably 1–2, carbon atoms, such as methyl, ethyl, propyl, isopropyl, butyl, t-butyl and the like. The term "lower alkyl" is used herein to describe the straight chain alkyl groups described inmmediately above. Preferably, cycloalkyl groups are monocyclic, bicyclic or tricyclic ring systems of 3–8, more preferably 3–6, ring members per ring, such as cyclopropyl, cyclopentyl, cyclohexyl, adamantyl and the like. Alkyl also includes a straight chain or branched alkyl group that contains or is interrupted by a cycloalkyl portion. The straight chain or branched alkyl group is attached at any available point to produce a stable compound. Examples of this include, but are not limited to, 4-(isopropyl)-cyclohexylethyl or 2-methyl-cyclopropylpentyl. A substituted alkyl is a straight chain alkyl, branched alkyl, or cycloalkyl group defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like.

"Alkenyl"—alone or in combination means a straight, branched, or cyclic hydrocarbon containing 2–20, preferably 2–17, more preferably 2–10, even more preferably 2–8, most preferably 2–4, carbon atoms and at least one, preferably 1–3, more preferably 1–2, most preferably one, carbon to carbon double bond. In the case of a cycloalkyl group, conjugation of more than one carbon to carbon double bond is not such as to confer aromaticity to the ring. Carbon to carbon double bonds may be either contained within a cycloalkyl portion, with the exception of cyclopropyl, or within a straight chain or branched portion. Examples of alkenyl groups include ethenyl, propenyl, isopropenyl, butenyl, cyclohexenyl, cyclohexenylalkyl and the like. A substituted alkenyl is the straight chain alkenyl, branched alkenyl or cycloalkenyl group defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, carboxy, alkoxycarbonyl, aryloxycarbonyl, heteroaryloxycarbonyl, or the like attached at any available point to produce a stable compound.

"Alkynyl"—alone or in combination means a straight or branched hydrocarbon containing 2–20, preferably 2–17, more preferably 2–10, even more preferably 2–8, most preferably 2–4, carbon atoms containing at least one, preferably one, carbon to carbon triple bond. Examples of alkynyl groups include ethynyl, propynyl, butynyl and the like. A substituted alkynyl refers to the straight chain alkynyl or branched alkenyl defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like attached at any available point to produce a stable compound.

"Alkyl alkenyl" refers to a group —R—CR'=CR''' R'''', where R is lower alkyl, or substituted lower alkyl, R', R''', R'''' may independently be hydrogen, halogen, lower alkyl, substituted lower alkyl, acyl, aryl, substituted aryl, hetaryl, or substituted hetaryl as defined below.

"Alkyl alkynyl" refers to a groups —RC≡CR' where R is lower alkyl or substituted lower alkyl, R' is hydrogen, lower alkyl, substituted lower alkyl, acyl, aryl, substituted aryl, hetaryl, or substituted hetaryl as defined below.

"Alkoxy" denotes the group —OR, where R is lower alkyl, substituted lower alkyl, acyl, aryl, substituted aryl, aralkyl, substituted aralkyl, heteroalkyl, heteroarylalkyl, cycloalkyl, substituted cycloalkyl, cycloheteroalkyl, or substituted cycloheteroalkyl as defined.

"Alkylthio" denotes the group —SR, $—S(O)_{n=1-2}—R$, where R is lower alkyl, substituted lower alkyl, aryl, substituted aryl, aralkyl or substituted aralkyl as defined herein.

"Acyl" denotes groups —C(O)R, where R is hydrogen, lower alkyl substituted lower alkyl, aryl, substituted aryl and the like as defined herein.

"Aryloxy" denotes groups —OAr, where Ar is an aryl, substituted aryl, heteroaryl, or substituted heteroaryl group as defined herein.

"Amino" denotes the group NRR', where R and R' may independently by hydrogen, lower alkyl, substituted lower alkyl, aryl, substituted aryl, hetaryl, or substituted hetaryl as defined herein or acyl.

"Amido" denotes the group —C(O)NRR', where R and R' may independently by hydrogen, lower alkyl, substituted lower alkyl, aryl, substituted aryl, hetaryl, substituted hetaryl as defined herein.

"Carboxyl" denotes the group —C(O)OR, where R is hydrogen, lower alkyl, substituted lower alkyl, aryl, substituted aryl, hetaryl, and substituted hetaryl as defined herein.

"Aryl"—alone or in combination means phenyl or naphthyl optionally carbocyclic fused with a cycloalkyl of preferably 5–7, more preferably 5–6, ring members and/or optionally substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like.

"Substituted aryl" refers to aryl optionally substituted with one or more functional groups, e.g., halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido and the like.

"Heterocycle" refers to a saturated, unsaturated, or aromatic carbocyclic group having a single ring (e.g., morpholino, pyridyl or furyl) or multiple condensed rings (e.g., naphthpyridyl, quinoxalyl, quinolinyl, indolizinyl or benzo[b]thienyl) and having at least one hetero atom, such as N, O or S, within the ring, which can optionally be unsubstituted or substituted with, e.g., halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido and the like.

"Heteroaryl"—alone or in combination means a monocyclic aromatic ring structure containing 5 or 6 ring atoms, or a bicyclic aromatic group having 8 to 10 atoms, containing one or more, preferably 1–4, more preferably 1–3, even more preferably 1–2, heteroatoms independently selected from the group O, S, and N, and optionally substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable aromatic ring is retained. Examples of heteroaryl groups are pyridinyl, pyridazinyl, pyrazinyl, quinazolinyl, purinyl, indolyl, quinolinyl, pyrimidinyl, pyrrolyl, oxazolyl, thiazolyl, thienyl, isoxazolyl, oxathiadiazolyl, isothiazolyl, tetrazolyl, imidazolyl, triazinyl, furanyl, benzofuryl, indolyl and the like. A substituted heteroaryl contains a substituent attached at an available carbon or nitrogen to produce a stable compound.

"Heterocyclyl"—alone or in combination means a non-aromatic cycloalkyl group having from 5 to 10 atoms in which from 1 to 3 carbon atoms in the ring are replaced by heteroatoms of O, S or N, and are optionally benzo fused or fused heteroaryl of 5–6 ring members and/or are optionally substituted as in the case of cycloalkyl. Heterocycyl is also intended to include oxidized S or N, such as sulfinyl, sulfonyl and N-oxide of a tertiary ring nitrogen. The point of attachment is at a carbon or nitrogen atom. Examples of heterocyclyl groups are tetrahydrofuranyl, dihydropyridinyl, piperidinyl, pyrrolidinyl, piperazinyl, dihydrobenzofuryl, dihydroindolyl, and the like. A substituted hetercyclyl contains a substituent nitrogen attached at an available carbon or nitrogen to produce a stable compound.

"Substituted heteroaryl" refers to a heterocycle optionally mono or poly substituted with one or more functional groups, e.g., halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Aralkyl" refers to the group —R—Ar where Ar is an aryl group and R is lower alkyl or substituted lower alkyl group. Aryl groups can optionally be unsubstituted or substituted with, e.g., halogen, lower alkyl, alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Heteroalkyl" refers to the group —R—Het where Het is a heterocycle group and R is a lower alkyl group. Heteroalkyl groups can optionally be unsubstituted or substituted with e.g., halogen, lower alkyl, lower alkoxy, alkylthio, acetylene, amino, amido, carboxyl, aryl, aryloxy, heterocycle, substituted heterocycle, hetaryl, substituted hetaryl, nitro, cyano, thiol, sulfamido and the like.

"Heteroarylalkyl" refers to the group —R—HetAr where HetAr is an heteroaryl group and R lower alkyl or substituted lower alkyl. Heteroarylalkyl groups can optionally be unsubstituted or substituted with, e.g., halogen, lower alkyl, substituted lower alkyl, alkoxy, alkylthio, acetylene, aryl, aryloxy, heterocycle, substituted heterocycle, hetaryl, substituted hetaryl, nitro, cyano, thiol, sulfamido and the like.

"Cycloalkyl" refers to a divalent cyclic or polycyclic alkyl group containing 3 to 15 carbon atoms.

"Substituted cycloalkyl" refers to a cycloalkyl group comprising one or more substituents with, e.g., halogen, lower alkyl, substituted lower alkyl, alkoxy, alkylthio, acetylene, aryl, aryloxy, heterocycle, substituted heterocycle, hetaryl, substituted hetaryl, nitro, cyano, thiol, sulfamido and the like.

"Cycloheteroalkyl" refers to a cycloalkyl group wherein one or more of the ring carbon atoms is replaced with a heteroatom (e.g., N, O, S or P).

"Substituted cycloheteroalkyl" refers to a cycloheteroalkyl group as herein defined which contains one or more substituents, such as halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Alkyl cycloalkyl" denotes the group —R-cycloalkyl where cycloalkyl is a cycloalkyl group and R is a lower alkyl or substituted lower alkyl. Cycloalkyl groups can optionally be unsubstituted or substituted with e.g. halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Alkyl cycloheteroalkyl" denotes the group —R-cycloheteroalkyl where R is a lower alkyl or substituted lower alkyl. Cycloheteroalkyl groups can optionally be unsubstituted or substituted with e.g. halogen, lower alkyl, lower alkoxy, alkylthio, amino, amido, carboxyl, acetylene, hydroxyl, aryl, aryloxy, heterocycle, substituted heterocycle, hetaryl, substituted hetaryl, nitro, cyano, thiol, sulfamido and the like.

The compounds of this invention can be prepared as outlined in schemes 1–5. Compounds having the general formula II:

Kato et. al. J. Org. Chem. 1997, 62, 6833–6841; Palladium Reagents and Catalysts-Innovations in Organic Synthesis, Tsuji, John Wiley and Sons, 1995) followed by deprotection with either TBAF or $NH_4F$ (Markiewicz et. al Tetrahedron Lett.(1988), 29, 1561). The preparation of compound 1 has been previously described (K. Kato et. al. J. Org. Chem. 1997, 62, 6833–6841) and is outlined in scheme 5. Compounds with general formula VI can be prepared as shown in Scheme 2. Compound III, which can be obtained by reacting II with 2,2-dimethoxypropane in presence of an

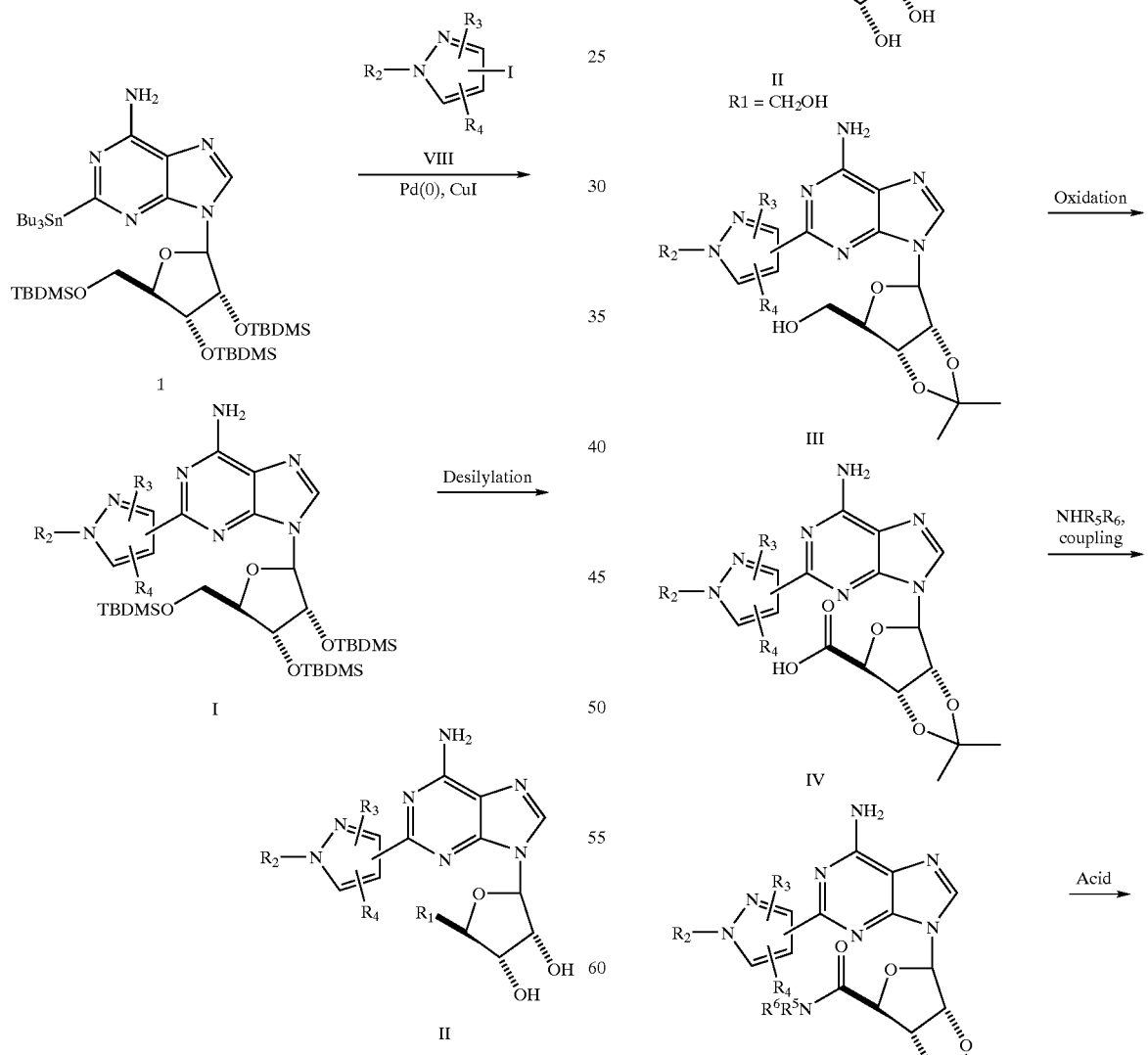

were prepared by the palladium mediated coupling of compound 1 with halo-pyrazoles represented by the formula VIII (scheme 4) in the presence or absence of copper salts (K.

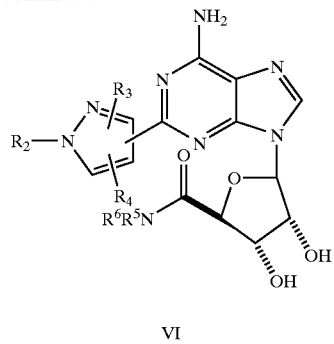

VI acid, can be oxidized to the carboxylic acid IV, based on structurally similar compounds, using potassium permanganate or pyridinium chlorochromate etc. (Jones et.al., J. Am. Chem. Soc.(1949), 71, 3994.; Hudlicky, Oxidations in organic chemistry, American Chemical Society, Washington D.C., 1990) to compound IV. Reaction of primary or secondary amine of the formula $NHR^5R^6$, and compound IV using DCC (Fujino et.al., Chem. Pharm. Bull. (1974), 22, 1857), PyBOP (J. Martinez et. al., J. Med. Chem. (1988), 28, 1967) or PyBrop (J. Caste et.al. Tetrahedron, (1991), 32, 1967) coupling conditions can afford compound V. Deprotection of compound V can be performed by heating with 80% aq. acetic acid (T. W. Green and P. G. M. Wuts, (1991), Protective Groups in Organic Synthesis, A, Wiley-Interscience publication) or with anhydrous HCl (4N) to obtain compound of the general formula VI.

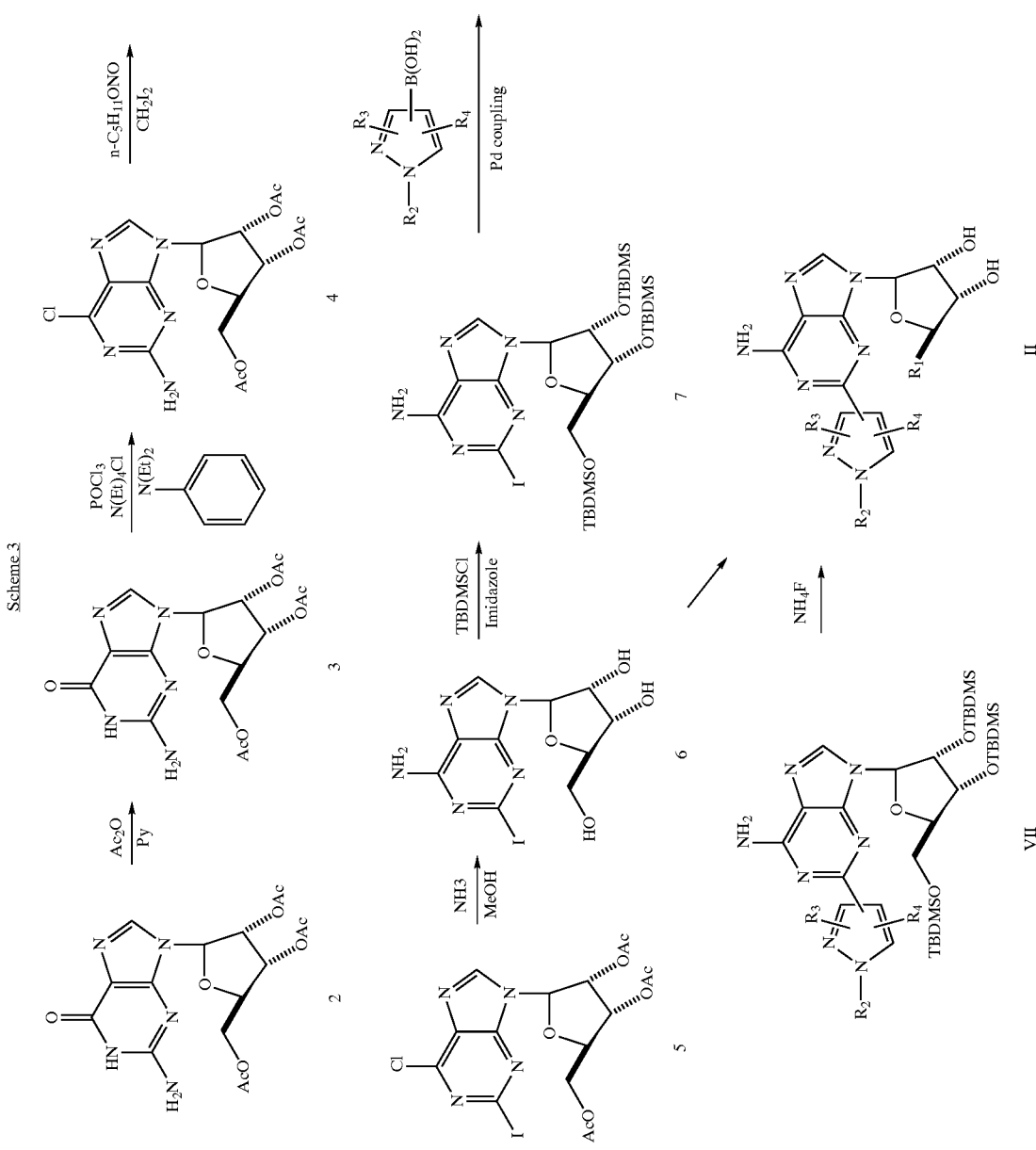

Alternatively, compounds with the general formula II can also be prepared by Suzuki type coupling as shown in scheme 3. 2-Iodoadenosine 6 can be prepared in four steps from guanosine 2 following literature procedures (M. J. Robins et.al. Can. J. Chem. (1981), 59, 2601–2607; J. F. Cerster et.al. Org. Synthesis,—242–243; V. Nair at. al., J. Org. Chem., (1988), 53, 3051–3057). Palladium mediated Suzuki coupling of 6 with appropriately substituted pyrazole-boronic acids XVII in presence of a base can provide final compounds with general formula II (A. Suzuki, Acc.Chem.Res) (1982), 15, 178). If necessary, 2', 3', 5' hydroxyls on 6 can be protected as TBDMS ethers prior to Suzuki coupling.

Compounds with the general formula VIII can be either commercially available or prepared following the steps shown in scheme 4. Condensation of 1,3-diketo compounds of the formula IX with hydrazine in an appropriate solvent can give pyrazoles with the general formula X (R. H. Wiley et. al. Org.Synthsis, Coll.Vol IV (1963), 351. These pyrazoles can be N-alkylated with various alkyl halides to give compounds of the formula XI which on iodination give 4-iodo derivatives with the general formula VIII (R. Huttel et.al. Justus Liebigs Ann.Chem.(1955), 593, 200).

Scheme 4

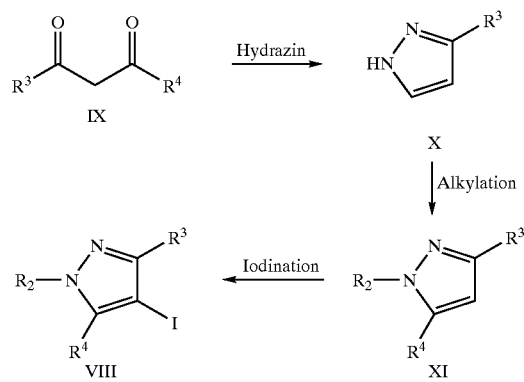

5-iodopyrazoles with the general formula XV can be prepared following the steps outlined in the scheme 5.

Scheme 5

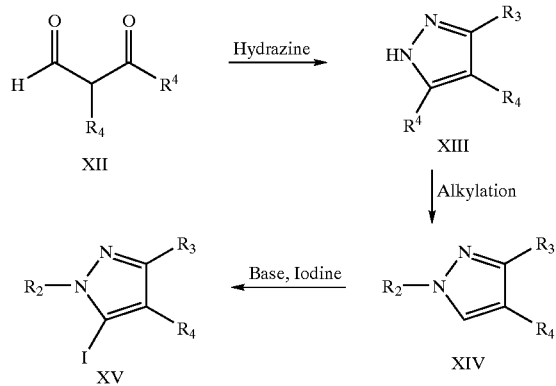

Condensation of 1,3-diketo compounds of the formula XII with hydrazine in an appropriate solvent can give pyrazoles with the general formula XIII. These pyrazoles can be N-alkylated with various alkyl halides to give compounds of the formula XIV. Abstraction of 5-H with a strong base followed by quenching with iodine can provide 5-iodo derivatives with general formula XV (F. Effenberger et. al. J. Org. Chem. (1984), 49, 4687).

4- or 5-iodopyrazoles can be transformed into corresponding boronic acids as shown in the scheme 6. Transmetallation with n-buLi followed by treatment with trimethylborate can give compounds with the general formula XVI which on hydrolysis can provide boronic acids with the general formula XVII (F. C. Fischer et.al. RECUEIL (1965), 84, 439).

Scheme 6

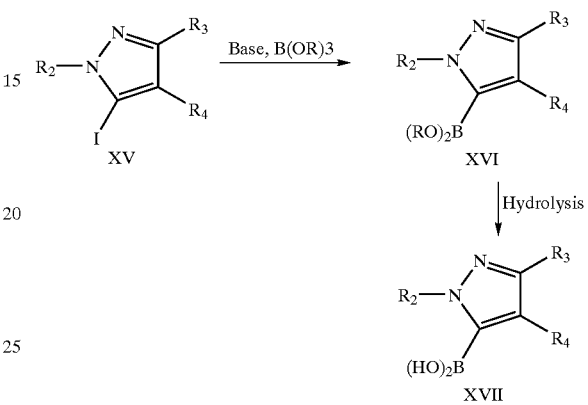

2-Stannyladenosine 1 was prepared in three steps from the commercially available 6-chloropurine riboside following literature procedure (K. Kato et.al., J. Org. Chem. (1997), 62, 6833–6841). Tri TBDMS derivative was obtained by treating 8 with TBDMSCl and imidazole in DMF. Lithiation with LTMP followed by quenching with tri n-butyltin chloride gave exclusively 2-stannyl derivative 10. Ammonolysis in 2-propanol gave 2-stannyladenosine 1. Stille coupling of 1 with 1-benzyl-4-iodopyrazole in presence of Pd(PPh3)4 and CuI resulted in 11 (K. Kato et.al., J. Org. Chem. (1997), 62, 6833–6841). Deprotecion of silyl groups on 2',3' and 5' hydroxyls with 0.5 M ammonium fluoride in methanol gave 12 in good yield (Scheme 7). Compounds 18–23 were prepared in similar manner. The methods used to prepare the compounds of this invention are not limited to those described above. Additional methods can be found in the following sources and are included by reference (J. March, Advanced Organic Chemistry; Reaction Mechanisms and Studies (1992), A Wiley Interscience Publications; and J. Tsuji, Palladium reagents and catalysts-Innovations in organic synthesis, John Wiley and Sons, 1995).

Scheme 7

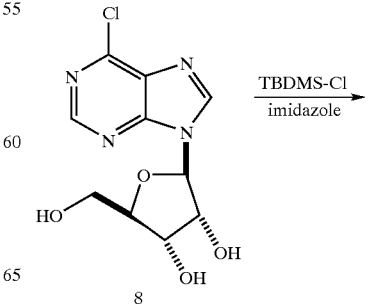

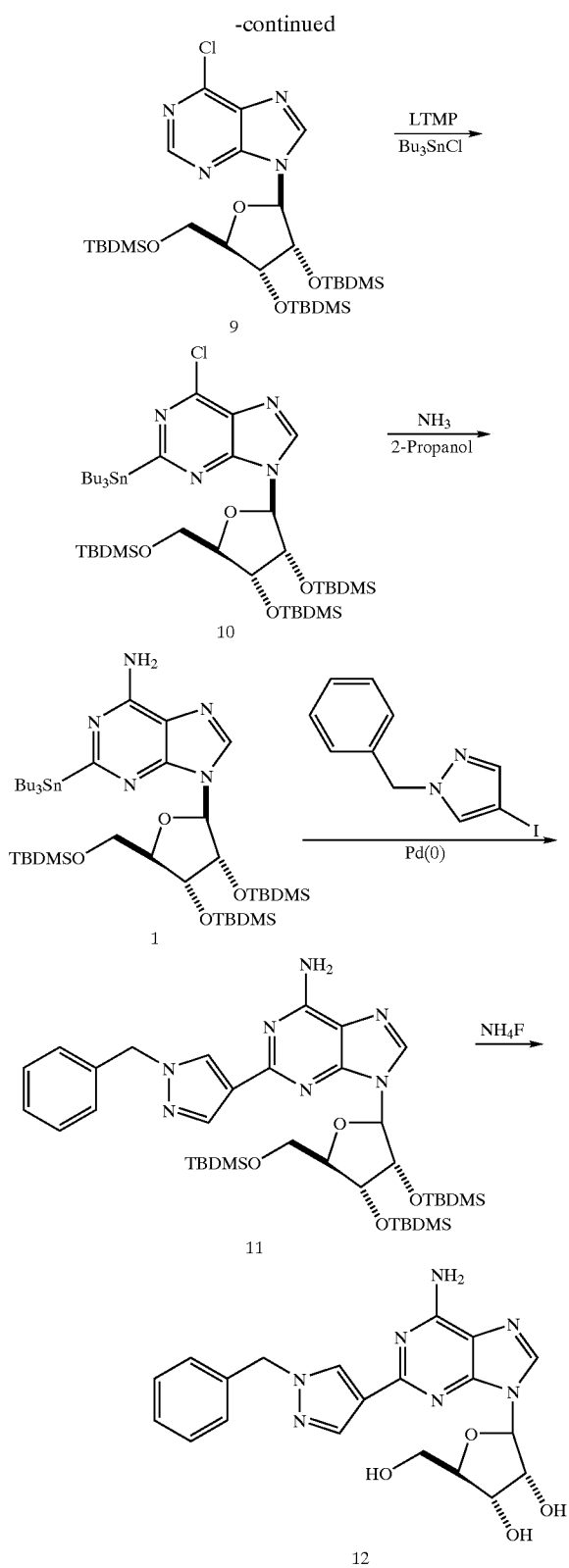

Compounds of this invention are useful in conjunction with radioactive imaging agents to image coronary activity. The compounds of this invention are $A_{2A}$ agonists that are believed to provide specific activation of adenosine $A_{2A}$ receptors in the coronary vessels as opposed to adenosine $A_1$ receptors in the atrium and AV-node and/or $A_{2B}$ receptors in peripheral vessels, thus avoiding undesirable side-effects. Upon. administration in a therapeutic amount, the compounds of this invention cause coronary blood vessels to vasodilate to induce coronary steal wherein healthy coronary vessels steal blood from unhealthy vessels resulting in lack of blood flow to heart tissues. Coronary imaging then identified coronary regions with healthy and unhealthy blood flow. Lower doses of the $A_{2A}$ agonists may provide beneficial coronary vasodilatation (less severe) in the treatment of chronic CAD.

As $A_{2A}$ agonists, the compounds of this invention are also useful in adjunctive therapy with angioplasty to induce dilation, inhibit platelet aggregation, and as a general anti-inflammatory agent. $A_{2A}$ agonists, such as the compounds of this invention, can provide the therapeutic benefits described above by preventing neutrophil activation (Purinergic Approaches in Experimental Therapeutics K. A. Jacobson and M. F. Jarvis 1997 Wiley, New York). The compounds of this invention are also effective against a condition called no-reflow in which platelets and neutrophils aggregate and block a vessel. As $A_{2A}$ agonists, the compounds of this invention are effective against no-reflow by preventing neutrophil and platelet activation (e.g., they are believed to prevent release of superoxide from neutrophils). As $A_{2A}$ agonists, the compounds of this invention are also useful as cardioprotective agents through their anti-inflammatory action on neutrophils. Thus, in situations when the heart will go through an ischemic state such as a transplant, they will be useful.

This invention also includes pro-drugs of the above-identified $A_{2A}$ agonists. A pro-drug is a drug which has been chemically modified and may be biological inactive at its site of action, but which will be degraded or modified by one or more enzymatic or in vivo processes to the bioactive form. The pro-drugs of this invention should have a different pharmacokinetic profile to the parent enabling improved absorption across the mucosal epithelium, better salt formulation and/or solubility and improved systemic stability. The above-identified compounds may be preferably modified at one or more of the hydroxyl groups. The modifications may be (1) ester or carbamate derivatives which may be cleaved by esterases or lipases, for example; (2) peptides which may be recognized by specific or non-specific proteinase; or (3) derivatives that accumulate at a site of action through membrane selection or a pro-drug form or modified pro-drug form, or any combination of (1) to (3) above.

The compositions may be administered orally, intravenously, through the epidermis or by any other means known in the art for administering a therapeutic agents. The method of treatment comprises the administration of an effective quantity of the chosen compound, preferably dispersed in a pharmaceutical carrier. Dosage units of the active ingredient are generally selected from the range of 0.01 to 100 mg/kg, but will be readily determined by one skilled in the art depending upon the route of administration, age and condition of the patient. This dose is typically administered in a solution about 5 minutes to about an hour or more prior to coronary imaging. No unacceptable toxicological effects are expected when compounds of the invention are administered in therapeutic amounts.

If the final compound of this invention contains a basic group, an acid addition salt may be prepared. Acid addition salts of the compounds are prepared in a standard manner in a suitable solvent from the parent compound and an excess of acid, such as hydrochloric, hydrobromic, sulfuric, phosphoric, acetic, maleic, succinic, or methanesulfonic. The hydrochloric salt form is especially useful. If the final compound contains an acidic group, cationic salts may be prepared. Typically the parent compound is treated with an excess of an alkaline reagent, such as hydroxide, carbonate or alkoxide, containing the appropriate cation. Cations such as Na+, K+, Ca+2 and NH4+ are examples of cations present in pharmaceutically acceptable salts. Certain of the compounds form inner salts or zwitterions which may also be acceptable.

Pharmaceutical compositions including the compounds of this invention, and/or derivatives thereof, may be formulated as solutions or lyophilized powders for parenteral administration. Powders may be reconstituted by addition of a suitable diluent or other pharmaceutically acceptable carrier prior to use. If used in liquid form the compositions of this invention are preferably incorporated into a buffered, isotonic, aqueous solution. Examples of suitable diluents are normal isotonic saline solution, standard 5% dextrose in water and buffered sodium or ammonium acetate solution. Such liquid formulations are suitable for parenteral administration, but may also be used for oral administration. It may be desirable to add excipients such as polyvinylpyrrolidinone, gelatin, hydroxycellulose, acacia, polyethylene glycol, mannitol, sodium chloride, sodium citrate or any other excipient known to one of skill in the art to pharmaceutical compositions including compounds of this invention. Alternatively, the pharmaceutical compounds may be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, teffa alba, magnesium stearate or stearic acid, talc, pectin, acacia, agar or gelatin. The carrier may also include a sustained release material such as glycerol monostearate or glycerol distearate, alone or with a wax. The amount of solid carrier varies but, preferably, will be between about 20 mg to about 1 gram per dosage unit. The pharmaceutical dosages are made using conventional techniques such as milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly or filled into a soft gelatin capsule. It is preferred that the compositions of this invention are administered as a solution either orally or intravenously by continuous infusion or bolus.

The Examples which follow serve to illustrate this invention. The Examples are intended to in no way limit the scope of this invention, but are provided to show how to make and use the compounds of this invention. In the Examples, all temperatures are in degrees Centigrade.

EXAMPLE 1

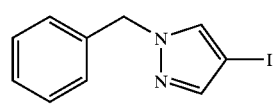

13

4-iodo-1-benzylpyrazole (13)

To a solution of 4-iodopyrazole (400 mg, 2 mmol) in DMF(4 mL) at 0 C. was added sodiumhydride (80 mg, 60% dispersion in mineral oil, 2 mmol) followed by benzyl bromide (342 mg, 2 mmol) and reaction micture was allowed to stir for 2 h. Reaction mixture was concentrated in vacuo and the residue was purified by column chromatography to give N-benzylpyrazole in almost quantitative yield. 1H NMR 5.29 (s, 2H), 7.18–7.28 (m,2H), 7.28–7.40 (m, 4H), 7.53 (s, 1H).

EXAMPLE 2

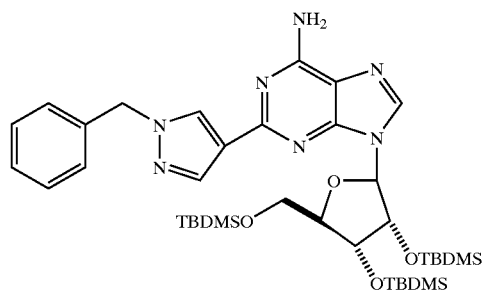

11

9-{(2R,3R,4R,5R)-3,4-bis(1,1,2,2-tetramethyl-1-silapropoxy)-5-[(1,1,2,2-tetramethyl-1-silapropoxy)methyl] oxolan-2-yl}-2-[1-benzylpyrazol-4yl]purine-6-ylamine (11)

A mixture of compound 1 (50 mg, 0.056 mmol), N-benzyl-4-iodopyrazole 13 (50 mg, 0.183 mmol), Pd(PPh3)4 (20 mg(15 mol %) and CuI (40 mg, 0.2 mmol) in DMF (1 mL) was stirred at 90 C. for 16 h. The reaction was concentrated in vacuo and the residue was purified by preparative thin layer chromatography (methylene chloride: methanol 10:1) to afford compound 11: 1H NMR(CDCl3) δ0.00(s, 3H, CH3), 0.01(s, 3H, CH3), 0.04(s, 3H, CH3), 0.07 (s, 3H, CH3), 0.11 (s, 3H, CH3), 0.14 (s, 3H, CH3), 0.78 (s, 9H, t-bu), 0.83 (s,9H, t-bu), 0.91 (s, 9H, t-bu), 3.80 (d, 1H), 4.05 (d, 1H), 4.11–4.12 (m, 1H), 4.33 (d, 1H), 4.50–4.52 (m, 1H), 5.35 (m, 2H), 5.65 (bs, 2H, D2O exchangeable), 6.05 (d, 1H), 7.28–7.40 (m, 5H), 7.98 (s, 1H), 8.18 (s, 1H), 8.22 (s, 1H).

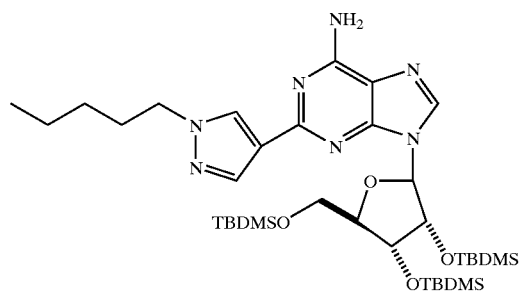

14

9-{(2R,3R,4R,5R)-3,4-bis(1,1,2,2-tetramethyl-1-silapropoxy)-5-[(1,1,2,2-tetramethyl-1-silapropoxy)methyl] oxolan-2-yl}-2-[1-pentylpyrazol-4-yl]purine-6-ylamine (14)

Compound 14 was prepared in the manner of compound 11 substituting 4-iodo-pentylpyrazole for 4-iodo-benzylpyrazole to afford compound 14: 1H NMR(CDCl3) 0.00(s, 3H, CH3), 0.01(s, 3H, CH3), 0.04(s, 3H, CH3), 0.07 (s, 3H, CH3), 0.11 (s, 3H, CH3), 0.14 (s, 3H, CH3), 0.78 (s, 9H, t-bu), 0.80 (t, 3H), 0.83 (s, 9H, t-bu), 0.91 (s, 9H, t-bu), 1.25–1.40 (m, 4H), 1.85–1.95 (m, 2H), 3.82 (d, 1H), 4.08 (d, 1H), 4.20–4.28 (m, 3H), 4.32–4.34 (m, 1H), 4.55–4.57 (m, 1H), 5.35 (m, 2H), 5.70 (bs, 2H, D2O exchangeable), 6.08 (d, 1H), 7.28–7.40 (m, 5H), 8.05 (s, 1H), 8.15 (s, 1H), 8.20 (s, 1H).

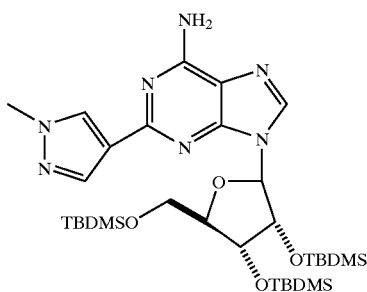

9-{(2R,3R,4R,5R)-3,4-bis(1,1,2,2-tetramethyl-1silapropoxy)-5-[(1,1,2,2-tetramethyl-1-silapropoxy)methyl]oxolan-2-yl}-2-[1-methylpyrazol-4-yl]purine-6-ylamine (15) Compound 15 was prepared in the manner of compound 11 substituting 4-iodo-methylpyrazole for 4-iodo-benzylpyrazole to afford compound 15: 1H NMR (CDCl3) 0.00 (s, 3H, CH3), 0.01 (s, 3H, CH3), 0.04 (s, 3H, CH3), 0.07 (s, 3H, CH3), 0.11 (s, 3H, CH3), 0.14 (s, 3 H, CH3), 0.78 (s, 9H, t-bu), 0.83 (s, 9H, t-bu), 0.91 (s, 9H, t-bu), 3.8 (d, 1H), 3.90 (s, 3H, N-CH3) 4.05 (d, 1H), 4.08–4.12 (m, 1H), 4.30–4.32 (m, 1H), 4.55–4.60 (m, 1H), 5.60 (bs, 1H, D2O exchangeable), 6.00–6.05 (m, 1H), 7.99 (s, 1H), 8.05 (s, 1H), 8.15 (s, 1H)

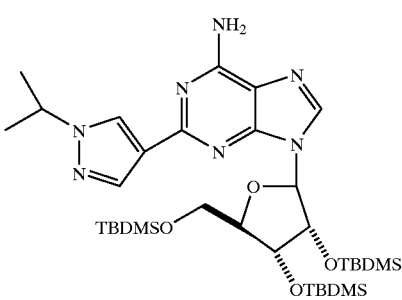

9-{(2R,3R,4R,5R)-3,4-bis(1,1,2,2-tetramethyl-1silapropoxy)-5-[(1,1,2,2-tetramethyl-1-silapropoxy)methyl]oxolan-2-yl}-2-[1-(1-methylethyl)pyrazol-4-yl]purine-6-ylamine (16)

Compound 16 was prepared in the manner of compound 11 substituting 4-iodo-(1-methylethyl)pyrazole for 4-iodo-benzylpyrazole to afford compound 16: 1H NMR(CDCl3) 0.00 (s, 3H, CH3), 0.01 (s, 3H, CH3), 0.04 (s, 3H, CH3), 0.07 (s, 3H, CH3), 0.11 (s, 3H, CH3), 0.14 (s, 3 H, CH3), 0.78 (s, 9H, t-bu), 0.83 (s, 9H, t-bu), 0.91 (s, 9H, t-bu), 1.55(d, 6H, C(CH3)2), 3.8 (d, 1H), 4.05 (d, 1H), 4.08–4.15 (m, 1H), 4.30–4.32 (m, 1H), 4.44–4.56 (m, 2H), 5.55(bs, 1H, D2O exchangeable), 6.05 (s, 1H), 8.05 (s, 1H), 8.10 (s, 1H), 8.2 (s, 1H)

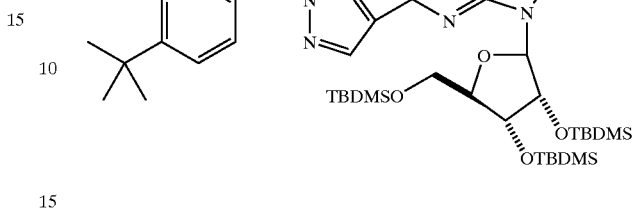

9-{(2R,3R,4R,5R)-3,4-bis(1,1,2,2-tetramethyl-1silapropoxy)-5-[(1,1,2,2-tetramethyl-1-silapropoxy)methyl]oxolan-2-yl}-2-[1-(4-t-butylbenzyl)pyrazol-4-yl]purine-6-ylamine (17)

Compound 17 was prepared in the manner of compound 11 substituting 4-iodo-(4-t-butylbenzyl)pyrazole for 4-iodo-benzylpyrazole to afford compound 17: 1H NMR(CDCl3) 0.00 (s, 3H, CH3), 0.01 (s, 3H, CH3), 0.04 (s, 3H, CH3), 0.07 (s, 3H, CH3), 0.11 (s, 3H, CH3), 0.14 (s, 3 H, CH3), 0.78 (s, 9H, t-bu), 0.83 (s, 9H, t-bu), 0.91 (s, 9H, t-bu), 1.30 (s, 9H, t-bu), 3.8 (d, 1H), 4.05 (d, 1H), 4.08–4.15(m, 1H), 4.30–4.32 (d, 1H), 4.47–4.49 (dd, 1H), 5.44 (bs, 1H, D2O exchangeable), 6.01 (d, J=3.6 Hz, 1H), 7.2 (d, J=2.0 Hz, 2H), 7.35 (d, J=2.0 Hz, 2H), 7.99 (s, 1H), 8.14 (s, 1H), 8.20 (s, 1H)

EXAMPLE 3

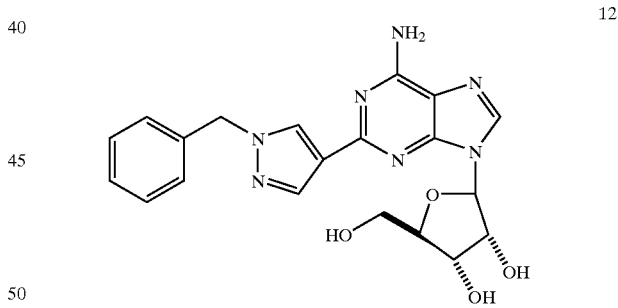

(4S,2R,3R,5R)-2-{6-amino-2-[1-benzylpyrazol-4-yl]purin-9-yl}-5-(hydroxymethyl)oxolane-3,4-diol (12)

A solution of triTBDMS derivative (25 mg, 0.035 mmol) in 0.5 M solution of NH4F in methanol (5 mL) was refluxed for 16 h. Reaction mixture was concentrated and residue was purified by preparative TLC (methanol-dichloromethane 9:1) to afford 12; 1H NMR (CD3OD) 3.65 (d, J=11.2 Hz, 1H), 3.81 (d, J=11.2 Hz, 1H), 4.18–4.19 (m, 1H), 4.26 (d, J=5.2 Hz, 1H), 4.78 (dd, 1H), 5.23 (s, 2H), 5.72 (d, J=7.2 Hz, 1H), 7.15–7.17 (m, 2H), 7.17–7.27 (m, 3H), 7.80 (s, 1H), 8.10 (s, 2H).

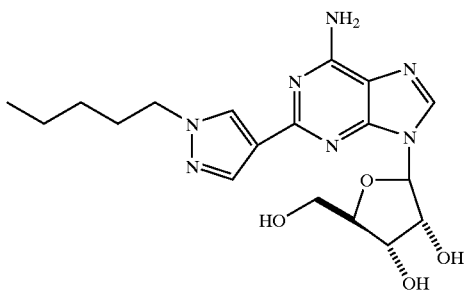

(4S,2R,3R,5R)-2-[6-amino-2-(1-pentylpyrazol-4-yl)purin-9yl]-5-(hydroxymetbyl)oxolane-3,4-diol (18)

Compound 18 was prepared in the manner of compound 12; 1H NMR (CD3OD) 4 0.8 (t, J=3.6 Hz, 3H), 1.20–1.26 (m, 4H), 1.76–1.80 (m, 2H), 3.67 (d, J=12.0 Hz, 1H), 3.85 (d, J=12.0 Hz, 1H), 4.03 (t, J=7.2 Hz, 2H), 4.19–4.20 (m, 1H), 4.28 (d, J=1.2 Hz, 1H), 4.78 (dd, 1H), 5.73 (d, J=7.2 Hz, 1H), 7.80 (s, 1H), 8.05 (s, 1H), 8.07 (s, 1H).

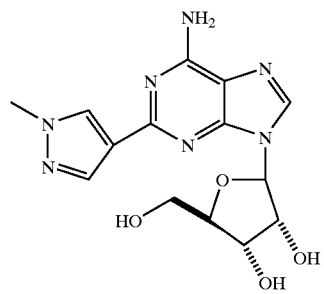

(4S,2R,3R,5R)-2-[6-amino-2-(1-methylpyrazol-4-yl)purin-9-yl]-5-(hydroxymethyl)oxolane-3,4-diol (19)

Compound 19 was prepared in the manner of compound 12; 1H NMR (CD3OD) 3.60 (d, J=9.2 Hz, 1H), 3.78 (s, 3H, N-CH3), 3.80 (d, J=9.2 Hz, 1H), 4.10–4.12 (m, 1H), 4.24 (d, J=1.4 Hz, 1H), 4.78 (dd, 1H), 5.69 (d, J=7.0 Hz, 1H), 7.80 (s, 1H), 7.98 (s, 1H), 8.01 (s, 1H).

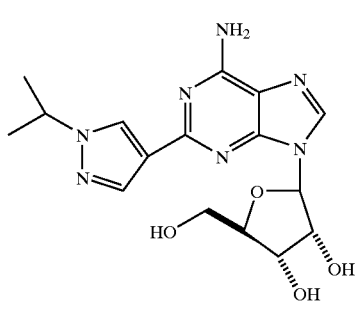

(4S,2R,3R,5R)-2-{6-amino-2-[1-(methylethyl)pyrazol-4-yl]purin-9-yl}-5-(hydroxymethyl)oxolane-3,4-diol (20)

Compound 20 was prepared in the manner of compound 12; 1H NMR (CD3OD) 1.41 (d, J=6.8 Hz, 6H), 3.66 (d, J=9.0 Hz, 1H), 3.80 (d, J=9.0 Hz, 1H), 4.16–4.18 (m, 1H), 4.25 (d, J=4.8 Hz, 1H), 4.40 (septet, 1H), 4.77 (dd, 1H), 5.71 (d, J=7.2 Hz, 1H), 7.80 (s, 1H), 8.03 (s, 1H), 8.13 (s, 1H).

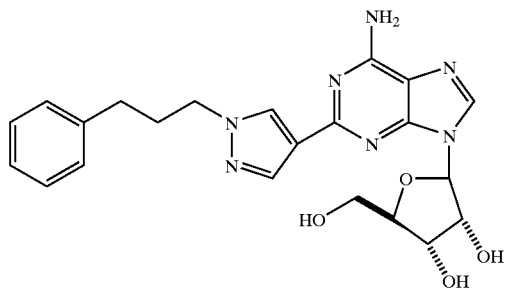

(4S,2R,3R,5R)-2-{6-amino-2-[-1-(3-phenylpropyl)pyrazol-4-yl]purin-9-yl}-5-(hydroxymethyl)oxolane-3,4-diol (21)

Compound 21 was prepared in the manner of compound 12; 1H NMR (CD3OD) 2.10 (t, J=6.7 Hz, 2H, CH2), 2.51 (t, J=6.7 Hz, 2H, CH2), 3.65 (d, J=9.2 Hz, 1H), 3.80 (d, J=9.2 Hz, 1H), 4.04 (t, J=6.7 Hz, 1H), 4.16–4.17 (m, 1H), 4.25 (d, J=1.2 Hz, 1H), 4.79 (dd, 1H), 5.71 (d, J=7.2 Hz, 1H), 7.05–7.07 (m, 2H), 7.16–7.24 (m, 3H), 7.80 (s, 1H), 8.06 (s, 1H), 8.08 (s, 1H).

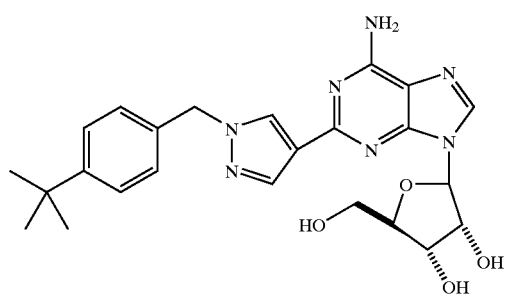

(4S,2R,3R,5R)-2-{6-amino-2-[1-(4-t-butylbenzyl)pyrazol-4-yl]purin-9-yl}-5-(hydroxymethyl)oxolane-3,4-diol (22)

Compound 22 was prepared in the manner of compound 12;1H NMR (CD3OD) 1.15 (s, 9h, t-bu) 3.55 (d, J=11.2 Hz, 1H), 3.75 (d, J=11.2 Hz, 1H), 4.18–4.19 (m, 1H), 4.26 (d, J=5.2 Hz, 1H), 4.65 (dd, 1H), 5.12 (s, 2H), 5.65 (d, J=7.2 Hz, 1H), 7.05 (d, 2H), 7.17 (d, 3H), 7.75 (s, 1H), 8.05 (s, 2H).

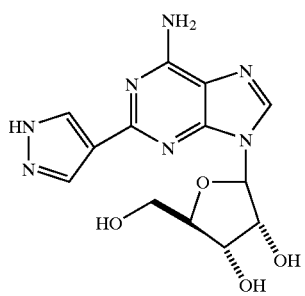

(4S,2R,3R,5R)-2-(6-amino-2-pyrazol-4-ylpurin-9-yl)-5-(hydroxymethyl)oxolane-3,4-diol (23)

Compound 23 was prepared in the manner of compound 12; 1H NMR (CD3OD) 3.75 (d, 1 H, 5'-CH), 3.90 (d, 1 H, 5'-CH), 4.15 (d, 2 H, 4'-CH) 4.35 (m, 1 H, 3'-CH), 4.85 (m, 1 H, 2'-CH), 5.95 (d, 1 H, 1'-CH), 8.20 (s, 1 H, 8-H), 8.25 (s, 2 H, Ar).

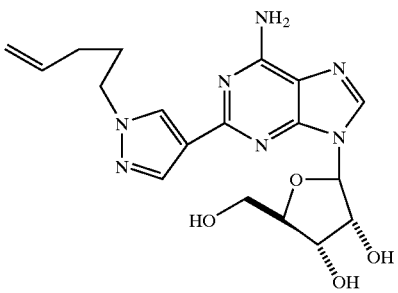

(4S,2R,3R,5R)-2-{6-amino-2-[1-pent-4-enylpyrazol-4-yl]purin-9-yl}-5-(hydroxymethyl)oxolane-3,4-diol 24

Compound 24 was prepared in the manner of compound 12; [MS 402 (M+1)]

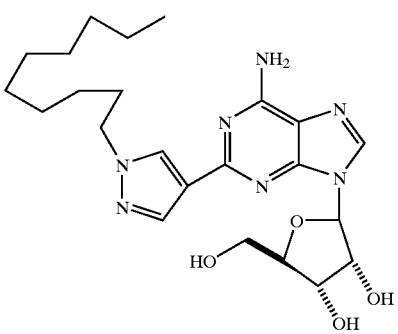

(4S,2R,3R,5R)-2-{6-amino-2-[1-decylpyrazol-4-yl]purin-9-yl}-5-(hydroxymethyl)oxolane-3,4-diol (25)

Compound 25 was prepared in the manner of compound 12; [MS 430 (M+1)]

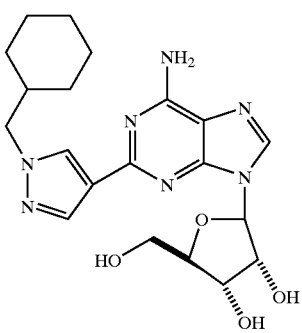

(4S,2R,3R,5R)-2-{6-amino-2-[1-(cyclohexylmethyl)pyrazol-4-yl]purin-9-yl}-5-(hydroxymethyl)oxolane-3,4-diol —26

Compound 26 was prepared in the manner of compound 12; [MS 474 (M+1)]

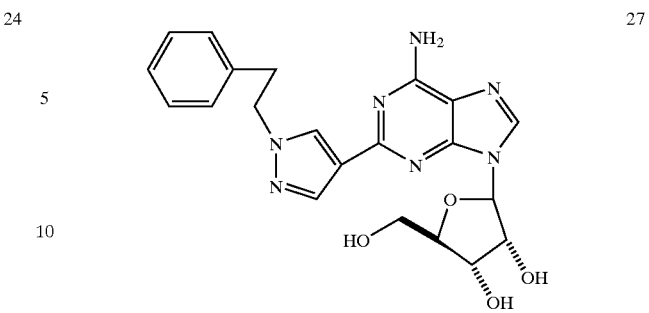

(4S,2R,3R,5R)-2-{6-amino-2-[1-(2-phenylethyl)pyrazol-4-yl]purin-9-yl}-5-(hydroxymethyl)oxolane-3,4-diol—27

Compound 27 was prepared in the manner of compound 12; [MS 438 (M+1)]

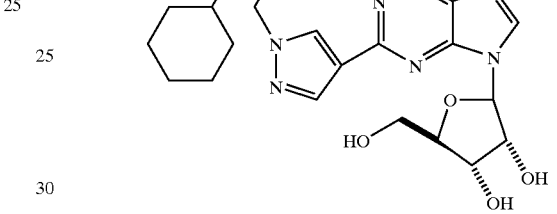

(4S,2R,3R,5R)-2-{6-amino-2-[1-(3-cyclohexylpropyl)pyrazol-4-yl]purin-9-yl}-5-(hydroxymethyl)oxolane-3,4-diol Compound 28 was prepared in the manner of compound 12; [MS 458 (M+1)]

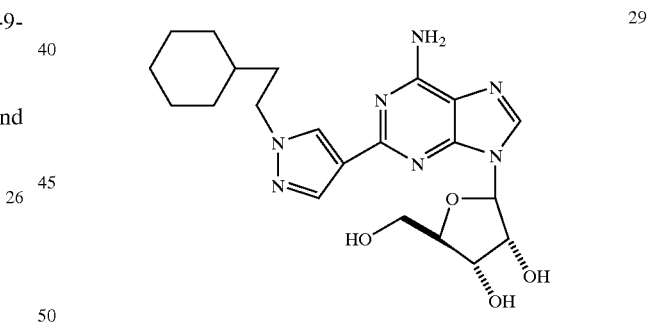

(4S,2R,3R,5R)-2-{6-amino-2-[1-(2-cyclohexylpropyl)pyrazol-4-yl]purin-9-yl}-5-(hydroxymethyl)oxolane-3,4-diol-29

Compound 29 was prepared in the manner of compound 12; [MS 444 (M+1)]

EXAMPLE 4

Compounds of this invention were assayed to determine their affinity for the A2A receptor in a pig striatum membrane prep. Briefly, 0.2 mg of pig striatal membranes were treated with adenosine deaminase and 50 mM Tris buffer (pH=7.4) followed by mixing. To the pig membranes was added 2 microL of serially diluted DMSO stock solution of the compounds of this invention at concentrations ranging from 100 microM to 10 nM or the control received 2 microL of DMSO alone, then the tritiated antagonist ZM 241385 in Tris buffer (50 mM, pH of 7.4) was added to achieve a final concentration of 2 nM. After incubation at 23 C. for 2 h, then the solutions were filtered using a membrane harvester using multiple washing of the membranes (3×). The filter disks were counted in scintillation cocktail affording the amount of displacement of tritiated ZM by the competitive binding compounds of this invention. Greater than a 5 point curve was used to generate IC50's and the number of experiments is indicated in the column marked in Table 1 below.

TABLE 1

| Compound Number | $A_{2a}$ Ki (nM) | n |
|---|---|---|
| 12 | 6674 ± 1121 | 3 |
| 18 | 7089 ± 780 | 3 |
| 19 | >10,000 | 1 |
| 20 | ~10,000 | 1 |
| 21 | 6133 ± 582 | 2 |
| 22 | 7680 | 1 |
| 23 | >100,000 | 1 |

EXAMPLE 5

The objective of this experiment was to determine the affinities and receptor binding selectivity of a compound of this invention for $A_1$, $A_{2A}$, $A_{2B}$ and $A_3$ adenosine receptors. Molecular cloning has identified and confirmed the existence of four subtypes of adenosine receptors (AdoRs), designated as $A_1$, $A_{2A}$, $A_{2B}$ and $A_3$AdoRs (Linden, 1994). These AdoR subtypes have distinct anatomical distributions, pharmacological properties and physiological functions (Shryock and Belardinelli, 1997). $A_1$ and $A_3$AdoRs couple to inhibitory G proteins ($G_i/_o$) and decrease the activity of adenylyl cyclase, whereas $A_{2A}$ and $A_{2B}$AdoRs increase intracellular cAMP content via coupling to stimulatory G proteins (Gs).

Ligands with high potency and tissue/organ selectivity for distinct adenosine receptor subtypes have therapeutic and diagnostic potentials for a variety of diseases (such as arrhythmias, ischemic heart diseases, asthma and Parkinson's disease) and are the focus of considerable research efforts by both academia and industry. Here we report the pharmacological and functional characterization of a series of novel adenosine analogues of this invention using mammalian cell lines expressing either endogenous AdoRs or recombinant human AdoRs.

Materials

Adenosine deaminase was purchased from Boehringer Manheim Biochemicals Indianapolis, Ind., U.S.A). [³H] ZM241385 (Lot No. 1) was purchased from Tocris Cookson Ltd (Langford, Bristol, UK). [³H]CPX (Lot No. 3329207) was from New England Nuclear (Boston, Mass., USA). CGS21680 (Lot No. SW-3R-84 and 89H4607), NECA (Lot No. OXV-295E), R-PIA (Lot No. WY-V-23), Rolipram and HEK-hA$_{2A}$AR membranes were obtained from Sigma-RBI (Natick, Mass.). WRC-0470 was prepared as described in the literature (K. Niiya et al., J. Med. Chem. 35: 4557–4561 (1992). Compound 18 and Compound 12 of this invention were synthesized and prepared as stock solutions (10 mmol/L) in DMSO.

Cell culture and membrane preparation-PC12 cells were obtained from the American Type Culture Collection and grown in DMEM with 5% fetal bovine serum, 10% horse serum, 0.5 mmol/L L-glutamine, 100 U/mL penicillin, 0.1 mg/mL streptomycin, and 2.5 μg/mL amphotericin. HEK-293 cells stably expressing recombinant human A$_{2B}$AdoRs (HEK-hA$_{2B}$AdoR) were grown in DMEM supplemented with 10% fetal bovine serum and 0.5 mg/mL G-418. CHOK1 cells stably expressing the recombinant human A$_1$AdoR (CHO-hA$_1$AdoR) and A$_3$AdoR (CHO-hA$_3$AdoR) were grown as monolayers on 150-mm plastic culture dishes in Ham's F-12 media supplemented with 10% fetal bovine serum in the presence of 0.5 mg/mL G-418. Cells were cultured in an atmosphere of 5% $CO_2$/95% air maintained at 37° C.

To make membranes, cells were detached from the culture plates into ice-cold 50 mmol/L Tris-HCI buffer (pH7.4). The cell suspensions were homogenized with Polytron at setting 4 for 30 seconds, and spun at 48,000 g for 15 minutes. The pellets were washed three times by re-suspension in ice-cold Tris-HCI buffer and centrifugation. The final pellet was re-suspended in a small volume of Tris-HCI, aliquoted and frozen at −80° C. until used for receptor binding assays. The protein concentration of membrane suspensions was determined using the Bradford method (Bio-Rad) with bovine serum as standards.

Competition Binding Assays-Competition assays were performed to determine the affinities ($K_i$) of the following unlabeled compounds (competing agents): Compounds WRC-0470, Compound 18, Compound 12, NECA, CGS 21680 and R-PIA for A$_1$AdoRs ([³H]DPCPX binding sites on CHO-hA$_1$AdoR cell membranes), A$_{2A}$AdoRs([³H]ZM241385 binding sites on PC12 and HEK-hA$_{2A}$AR cell membranes), A$_{2B}$AdoR ([³H]DPCPX binding sites on HEK-hA$_{2B}$AdoR cell membranes) and A$_3$AdoR ([¹²⁵I]ABMECA binding sites on CHO-hA$_3$AdoR cell membrane). Membrane suspensions were incubated for 2 hours at room temperature in 50 mmol/L Tris-HCI buffer (pH 7.4) containing ADA (1 U/mL), Gpp(NH)p (100 μM), radioligand {either [³H]ZM241385 (~1.5 to 5 nmol/L), [³H]DPCPX (~2.5 to 3.0 nmol/L for A$_1$ and 30 nM for A$_{2B}$) or [¹²⁵I]ABMECA (1 nM)} and progressively higher concentrations of the competing agents. At the end of incubation, bound and free radioligands were separated by filtration through Whatman GF/C glass fiber filters using a Brandel tissue harvester (Gaithersburg, Md.). Triplicate determinations were performed for each concentration of the competing agent.

Study Design (Protocols)

The affinity ($K_i$) of various CVT compounds for the A$_1$ and A$_{2A}$ adenosine receptor were determined by their potency to compete for [³H]CPX (A$_1$) or [³H]ZM241385 (A$_{2A}$) binding sites on membranes derived from CHO-hA$_1$AdoR, PC12 or HEK-HA$_{2A}$AdoR cells. R-PIA and CGS21680, agonists that are selective for A$_1$ and A$_{2A}$ respectively, and NECA, a non-selective AdoR agonist were used as controls. To facilitate comparison and avoid the complication of multiple affinity states due to receptor coupling to G-proteins, the competition binding studies were carried out in the presence of Gpp (NH) p (100 μM) to uncouple receptors from G-proteins. The affinity of selected compounds for A$_{2B}$ and A$_3$ receptors were assessed by their potencies to compete for [³H] CPX (A$_{2B}$) and [¹²⁵I] ABMECA (A3) binding sites on membranes derived from HEK-hA$_{2B}$AdoR and CHO-hA$_3$AdoR cells, respectively.

The functional potency and selectivity of these drugs for A$_{2A}$ vs. A$_{2B}$AdoRs were assessed by determining their effects on A$_{2A}$ or A$_{2B}$-mediated cAMP accumulation in PC 12 and HEK-293 cells, respectively. In these experiments, CGS21680 and NECA were used as positive controls.

Results

The affinity ($K_i$) of WRC-0470, Compound 18, and Compound 12 for human A$_1$, rat and human A$_{2A}$AdoRs, as determined by competition binding studies are summarized in Table 2, below. With the exception of Compound 12, all compounds show moderate selectivity for human A$_{2A}$ versus A$_1$ receptor.

TABLE 2

Binding Affinities of Adenosine Receptor Agonists for $A_{2A}$AdoRs and $A_1$AdoRs $K_i$/ nmol/L ($pK_i$ ± SEM)

| | HEK-hA$_{2A}$AR Cells | | CHO-hA$_1$AR | |
|---|---|---|---|---|
| | Binding Affinity | n | Binding Affinity | n |
| WRC-0470 | 272 (6.55 ± 0.04) [0.83 ± 0.07] | 6 | 7278 (5.16 ± 0.09) [1.13 ± 0.21] | 3 |
| Compound 18 | 2895 (5.54 ± 0.03) [0.83 ± 0.07] | 3 | 5836 (5.24 ± 0.04) [1.01 ± 0.06] | 3 |
| Compound 12 | 13651 (4.87 ± 0.02) [0.75 ± 0.13] | 3 | 6350 (5.22 ± 0.11) [0.93 ± 0.03] | 3 |
| CGS21680 | 609 (6.22 ± 0.06) {0.65 ± 0.07) | 3 | >3540 (5.47 ± 0.20) | 3 |
| NECA | 360 (6.45 ± 0.06) [0.83 ± 0.08] | 3 | 328 (6.49 ± 0.06) [0.88 ± 0.03] | 3 |
| R-PIA | 1656 (5.78 ± 0.02) [1.05 ± 0.02) | 3 | 477 (6.35 ± 0.11) [1.03 ± 0.08) | 3 |

The results of this Experiment show that Compound 16 is a low affinity $A_{2A}$ agonist.

EXAMPLE 6

The objective of this Example was to characterize pharmacologically the effects of Compounds 12 and 18 of this invention on coronary artery conductance. Specifically, the experiments was designed to determine the potency of Compounds 12 and 18 and compared their potencies to that of adenosine and other selected $A_{2A}$ AdoR agonists.

In the heart, the $A_{2A}$ adenosine receptor mediates the coronary vasodilation caused by adenosine, whereas the $A_1$ receptor mediates the cardiac depressant actions of adenosine, such as the negative chronotropic and dromotropic (AV block) effects.

Several potent and selective ligands, both agonists and antagonists, for the A1 and $A_{2A}$ AdoRs have been synthesized. In the heart agonists of $A_1$ AdoRs have been proposed to be useful as antiarrhythmic agents, whereas agonists of $A_{2A}$ AdoRs are being developed for selective coronary vasodilation.

A series of adenosine derivatives targeted for selective activation of $A_{2A}$ adenosine receptor ($A_{2A}$ AdoR) were synthesized for the purposes of developing coronary vasodilators. More specifically, in this study we report on the effect of a series of novel $A_{2A}$ AdoR agonists on coronary artery conductance (vasodilation) in rat and guinea pig isolated perfused hearts.

Materials

Rats (Sprague Dawley) and Guinea pigs (Hartley) were purchased from Simonsen and Charles Rivers, respectively. WRC-0470 was prepared as described in the literature (K. Niiya et al., J. Med. Chem. 35: 4557–4561 (1992). Compound 12 and Compound 18 of this invention were prepared as described above. CGS 21680 (Lot No. 89H4607) and adenosine (Lot No.123HO94) were purchased from Sigma. Krebs-Henseleit solution was prepared according to Standard Methods, and 0.9% saline was purchased from McGraw, Inc. (Lot No.J8B246).

Methods

Adult Sprague Dawley rats and Hartley guinea pigs of either sex weighing from 230 to 260 grams and 300 to 350 grams, respectively were used in this study. Animals were anesthetized by peritoneal injection of a cocktail containing ketamine and xylazine (ketamine 100 mg, xylazin 20 mg/ml). The chest was opened and the heart quickly removed. The heart was briefly rinse in ice-cold Krebs-Henseleit solution (see below), and the aorta cannulated. The heart was then perfused at a flow rate of 10 ml/min with modified Krebs-Henseleit (K-H) solution containing NaCl 117.9, KCl 4.5, CaCl$_2$ 2.5, MgSO$_4$ 1.18, KH$_2$PO$_4$ 1–18, pyruvate 2.0 mmo/L. The K-H solution (pH 7.4) was gassed continuously with 95% O$_2$ and 5% CO$_2$ and warmed to 35±0.50 C. The heart was electrically paced at a fixed cycle length of 340 ms (250 beats/min) using a bipolar electrode place on the left atrium. The electrical stimuli were generated by a Grass stimulator (Model S48, W. Warwick, R.I.) and delivered through a Stimuli Isolation Unit (Model SIU5, Astro-Med, Inc., NY) as square-wave pulses of 3-msec in duration and amplitude of at least twice the threshold intensity.

Coronary perfusion pressure (CPP) was measured using a pressure transducer, connected to the aortic cannula via a T-connector positioned approximately 3 cm above the heart. Coronary perfusion pressure was monitored throughout the experiment and recorded either on a chart recorder (Gould Recorder 2200S) or a computerized recording system (PowerLab/4S, ADinstruments Pty Ltd, Australia). Only hearts with CPP ranging from 60 to 85 mmHg (in the absence of drugs) were used in the study. Coronary conductance (in ml/min/mmHg) was calculated as the ratio between coronary perfusion rate (10 ml/min) and coronary perfusion pressure.

In experiments in which $A_1$ adenosine receptor-mediated negative dromotropic effect was measured, atrial and ventricular surface electrograms were recorded during constant atrial pacing. The effect of various adenosine receptor agonists on atrioventricular conduction time was determined as described previously by Jenkins and Belardinelli Circ. Res. 63: 97–116 (1988).

Stock solutions of the compound of this invention (5 mM) and CGS 21680 (5 mM) were prepared in dimethyl sulfoxide (DMSO) purchased from Aldrich, PS 04253MS. A stock solution of adenosine (1 mg/ml) was prepared in saline. One concentration was made from the stock solution by dilution into saline to yield solution of either 2×10$^{-4}$ or 2×10$^{-5}$ M. These solutions were injected into the perfusion line of the apparatus as boluses of 20 μl. In some experiments the solutions were placed into a 30 ml glass syringe and the drugs were infused at rates necessary to achieve the desired perfusate concentrations (e.g, 10, 100 nM, etc).

Coronary vasodilation of $A_{2A}$ adenosine receptor agonists

Concentration-response relationships for the effect of the compounds of this invention (0.1 to 400 nM) and CGS21680 (0.1 to 10 nM) to increase coronary conductance were obtained. After recording control measurements of coronary perfusion pressure, progressive higher concentrations of the adenosine receptor agonists were administered until maximal coronary vasodilation was observed. The steady-state responses to each concentration of adenosine receptor agonists were recorded. In each heart of this series (4 to 6 hearts for each agonist) only one agonist and one concentration-response relationship was obtained.

Results

In isolated perfused hearts (n=36 rats and 18 guinea pigs) paced at constant atrial cycle length of 340 msec, adenosine, CGS21680, WRC0470, and Compounds 12 and 18 of this invention caused a concentration-dependent increase in coronary conductance. CGS21680 and WRC0470 were the most potent agonists of this series. Compounds 12 and 18 were about as potent as adenosine in increasing coronary conductance. It is worth noting that all agonists were several fold more potent coronary vasodilators in rat than guinea pig hearts.

TABLE 3

Potency of Adenosine and $A_{2A}$ Adenosine Receptor Agonists to Increase Coronary Conductance in Rat and Guinea Pig Isolated Perfused Hearts

| | | Potency ($EC_{50}$) | |
|---|---|---|---|
| Agonist | n | Rat | Guinea Pig |
| Compound 18 | 3 | 67.9 ± 16.7 | 203.0 ± 6.0 |
| Adenosine | 4 | 59.2 ± 6.4 | 86.0 ± 0.5 |
| CGS21680 | 4 | 0.5 ± 0.1 | 1.7 ± 0.4 |
| WRC0470 | 3 | 0.6 ± 0.2 | 2.4 ± 1.1 |

EXAMPLE 7

The objective of this Example was to determine the functional selectivity of Compound 18 to cause coronary vasodilation. Specifically, the potencies of Compound 18 to cause coronary vasodilation ($A_{2A}$ AdoR response) and prolongation of A-V nodal conduction time ($A_1$ AdoR response) were determined in rat and guinea pig hearts.

Materials

Sprague Dawley rats were purchased from Simonsen. Hartley guinea pigs were purchased from Charles River. Compound 18 was prepared as described above. CVT-510-2-{6-[((3R)oxolan-3-yl)amino]purin-9-yl}(4S,3R,5R)-5-(hydroxymethyl)oxolane-3,4-diol was prepared in accordance with the sythesis method disclosed in U.S. Pat. No. 5,789,416, the specification of which is incorporated herein by reference. Ketamine was purchased from Fort Dodge Animal Health (Lot No. 440444) and xylazine from Bayer (Lot No. 26051 A). Krebs-Henseleit solution was prepared according to the standard methods, and 0.9% sodium is chloride was purchased from McGraw, Inc. (Lot No. J8B246).

Isolated Perfused Heart Preparation

Rats and guinea pigs, of either sex weighing from 230 to 260 grams and 300 to 350 grams, respectively, were used in this study. Animals were anesthetized by peritoneal injection of a cocktail containing ketamine and xylazine (ketamine 100 mg, xylazine 20 mg/ml). The chest was opened and the heart quickly removed. The heart was briefly rinse in ice-cold Krebs-Henseleit solution (see below), and the aorta cannulated. The heart was then perfused at a flow rate of 10 ml/min with modified Krebs-Henseleit (K-H) solution containing NaCl 117.9, KCl 4.5, $CaCl_2$ 2.5, $MgSO_4$ 1.18, $KH_2PO_4$ 1.18, pyruvate 2.0 mmo/L. The K-H solution (pH 7.4) was gassed continuously with 95% $O_2$ and 5% $CO_2$ and warmed to 35±0.5° C. The heart was electrically paced at a fixed cycle length of 340 ms (250 beats/min) using a bipolar electrode place on the left atrium. The electrical stimuli were generated by a Grass stimulator (Model S48, W. Warwick, R.I.) and delivered through a Stimuli Isolation Unit (Model SIU5, Astro-Med, Inc., NY) as square-wave pulses of 3-msec in duration and amplitude of at least twice the threshold intensity.

Coronary perfusion pressure (CPP) was measured using a pressure transducer, connected to the aortic cannula via a T-connector positioned approximately 3 cm above the heart. Coronary perfusion pressure was monitored throughout the experiment and recorded either on a chart recorder (Gould Recorder 2200S) or a computerized recording system (PowerLab/4S, ADInstruments Pty Ltd, Australia). Only hearts with CPP ranging from 60 to 85 mmHg (in the absence of drugs) were used in the study. Coronary conductance (in ml/min/mmHg) was calculated as the ratio between coronary perfusion rate (10 ml/min) and coronary perfiision pressure.

$A_1$ adenosine receptor-mediated depression of A-V nodal conduction time (negative dromotropic effect) was measured. Atrial and ventricular surface electrograms in rats and His bundle electrogram in guinea pigs, were recorded during constant atrial pacing. The effects of Compound 18 on atrioventricular conduction time and stimulus-to-His-bundle (S-H interval) were determined as described previously by Jenkins and Belardinelli (1988).

The effects of Compound 18 on coronary conductance ($A_{2A}$ effect) and atrioventricular conduction time or stimulus-to-His-bundle (S-H) interval ($A_1$ effect) was then determined. Hearts were instrumented for continuous recording of coronary perfusion pressure ($A_{2A}$ response) and atrioventricular (A-V) conduction time or S-H interval ($A_1$ response). In each experiment, concentration-response relationship of Compound 18 (n=5 rats, 5 guinea pigs) to increase coronary conductance and to prolong A-V conduction time or S-H interval was determined. After control measurements of CPP and A-V conduction time or S-H interval were made, progressive higher concentrations of Compound 18 was administered until maximal coronary vasodilation and A-V nodal conduction time or S-H interval prolongation were achieved. In separate rat hearts (n=4), the effect of various concentrations (100–400 nM) of CVT510 (Insert chemical name), an $A_1$ adenosine agonist (Snowdy et al, 1999), on A-V nodal conduction time was determined and compared to that of Compound 18 (0.1–30 $\mu$M).

Figure 2:
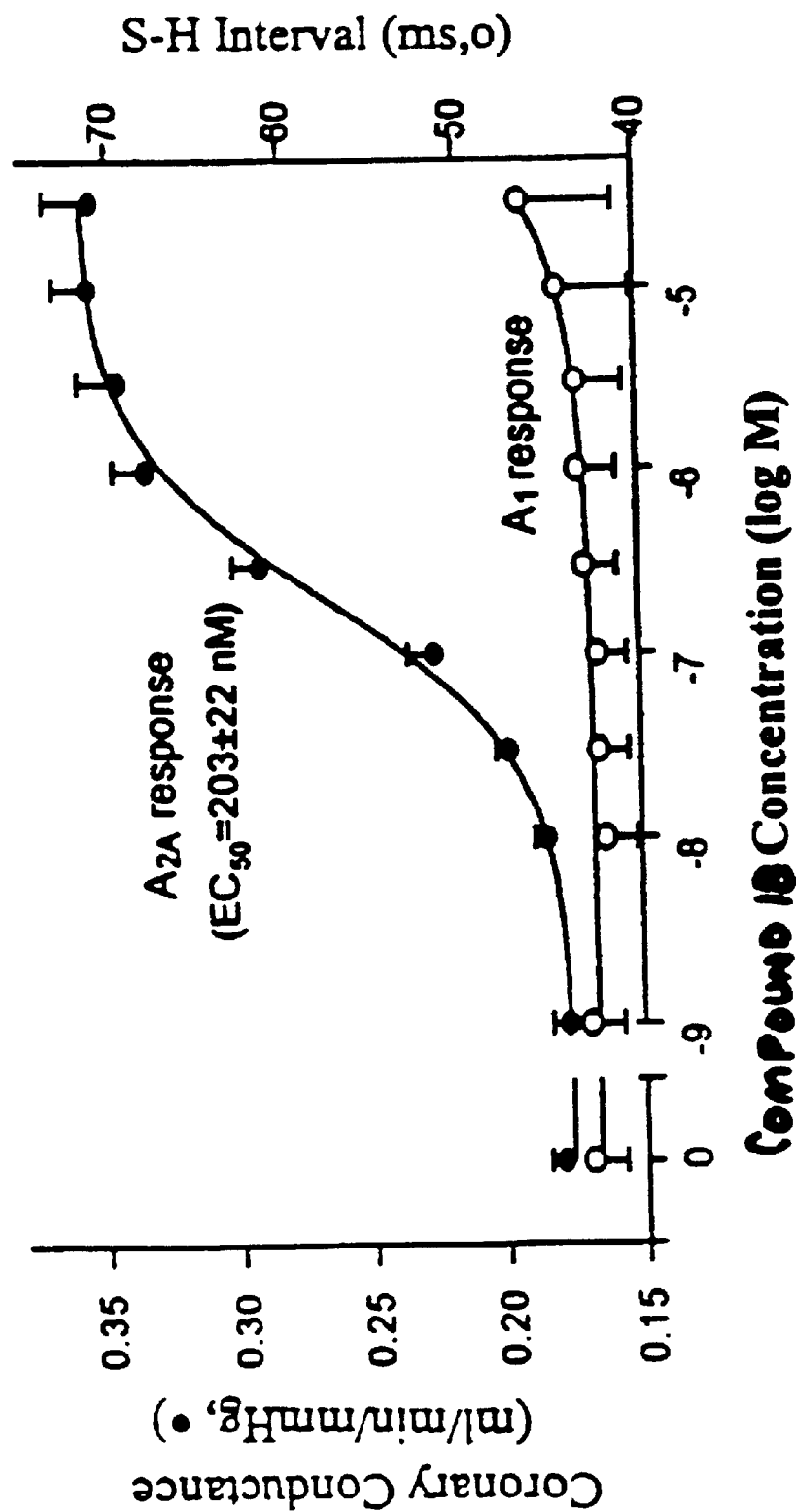
FIG. 2 is a concentration response curve for the $A_1$ adenosine receptor (AdoR)-mediated negative dromotropic (AV conduction time) and $A_{2A}$ AdoR-mediated vasodialator (increase coronary conductance) effects of Compound 18 in guinea pig isolated perfused hearts. Symbols and error bars indicate means±SEM of single determination from each of four hearts. $EC_{50}$ value (potency) is the concentration of Compound 18 that causes 50% of maximal response.
Figure 3:
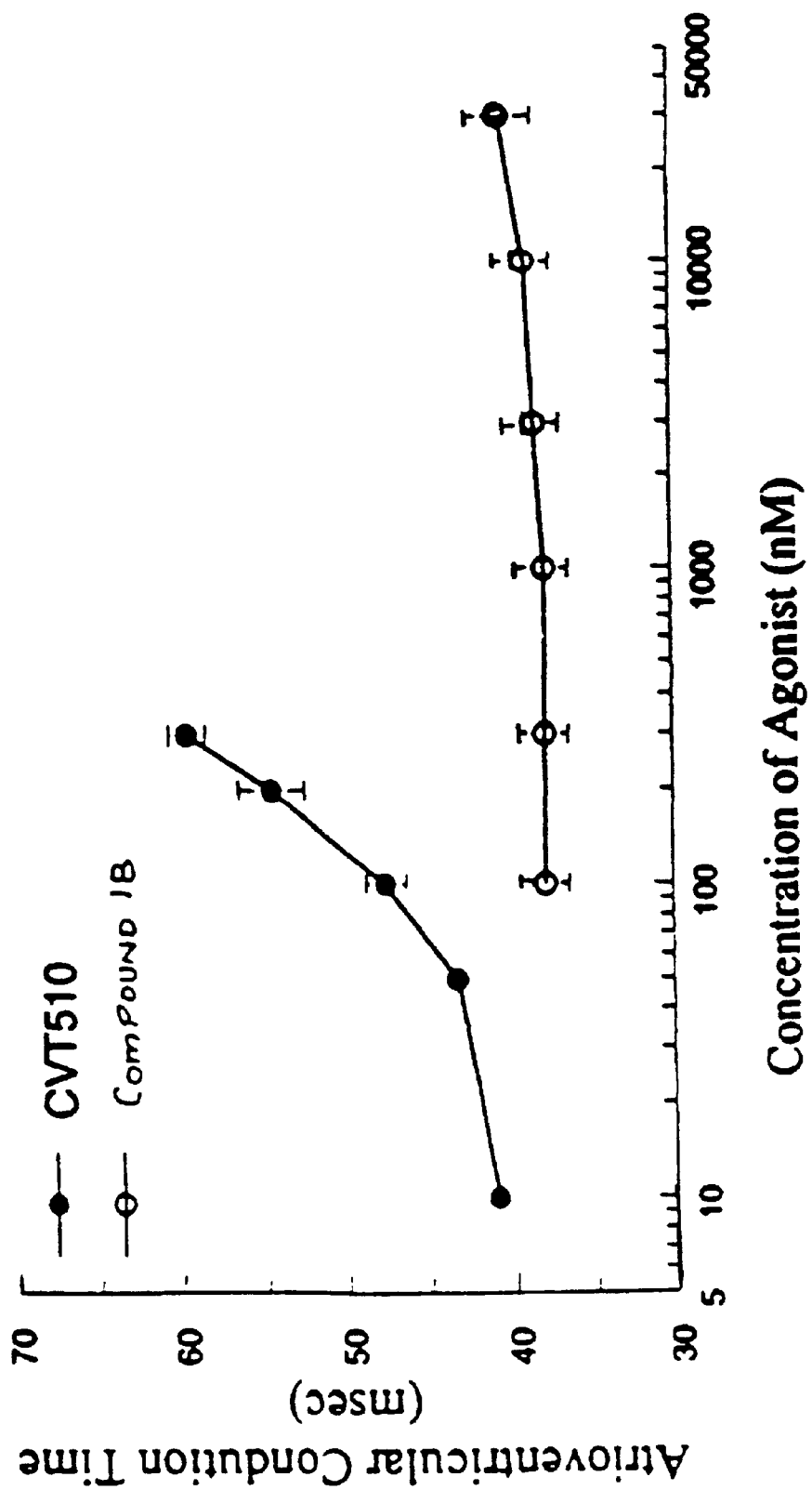
FIG. 3 is a plot of the effect of CVT510, an $A_1$ adenosine receptor agonist and Compound 18 of this invention, an $A_{2A}$ adenosine receptor agonist on atrioventricular (AV) conduction time in rat isolated perfused hearts.

The concentration-response curves for Compound 18 to increase coronary artery conductance and to prolong A-V nodal conduction time or S-H internal are shown in FIGS. 1 and 2. In both rat and guinea pig, Compound 18 increased coronary conductance in a concentration dependent manner. The potencies ($EC_{50}$ values) for Compound 18 to increase coronary conductance in rat hearts was 68.9±9.6 nM, and in guinea pig hearts was 203±22 nM. In contrast, the effect of this agonist on S-H interval was somewhat variable between rat and guinea pig hearts. In rat hearts Compound 18 did not prolong A-V nodal conduction time (FIG. 1), whereas the $A_1$ AdoR agonist CVT510 significantly prolonged the A-V nodal conduction time (FIG. 3). Compound 18 at concentrations at high as 50 $\mu$M caused no prolongation of S-H interval in guinea pig hearts (FIG. 2).

The results indicate that Compound 18 is a coronary vasodilator ($A_{2A}$ AdoR-mediated effect) devoid of negative dromotropic effect ($A_1$ AdoR-mediated effect) in rat hearts. In guinea pig hearts, Compound 18 caused no negative dromotropic effect. In both species (rat and guinea pig) Compound 18 causes maximal coronary vasodilation at concentrations that do not cause prolongation of A-V nodal conduction time, i.e., without negative dromotropic effect. It was also observed that Compound 18 has a greater affinity (i.e., >2-/>-13-fold) for $A_{2A}$ than $A_1$ AdoR and that there is a markedly greater receptor reserve for $A_{2A}$ AdoR-mediated coronary vasodilation than for $A_1$ AdoR-mediated negative dromotropic effect.

EXAMPLE 8

The present study was designed to test the hypothesis that there is an inverse relationship between the affinity ($K_i$ or $pK_i$) and duration of action of $A_{2A}$ adenosine receptors (AdoR). Specifically, the aims of the study were to determine the relationship between the duration of the coronary vasodilation caused by a selected series of high and low affinity $A_{2A}$ AdoR agonists in rat isolated hearts and anesthetized pigs; and the affinity of these agonists for $A_{2A}$ AdoRs in pig striatum.

Materials: Rats (Sprague Dawley) were purchased from Simonen. Farm pigs were obtained from Division of Laboratory Animal Resources, University of Kentucky. Compound 12, Compound 18, Compound 21, and Compound 13 of this invention were prepared as described in the methods above. YT-0146 was prepared as described in U.S. Pat. No.

4,956,345, the specification of which is incorporated herein by reference. WRC-0470 was prepared as described in the literature (K. Niiya et al., J. Med. Chem. 35: 4557–4561 (1992). CGS21680 was purchased from Research Biochemicals, Inc. and Sigma and R-PIA (Lot No. WY-V-23) was purchased from Research Biochemicals, Inc. HENECA was a gift from Professor Gloria Cristalli of University of Camerino, Italy.

Anesthetic agents: Ketamine was purchased from Fort Dodge Animal Health. Xylazine was purchased from Bayer. Sodium pentobarbital was purchased from The Butler Co. Phenylephrine was purchased from Sigma. DMSO was purchased from Sigma and American Tissue Type Collections. Krebs-Henseleit solution was prepared according to standard methods, and 0.9% saline was purchased from McGraw, Inc.

Rat isolated perfused heart preparation

Adult Sprague Dawley rats of either sex weighing from 230 to 260 grams were used in this study. Animals were anesthetized by peritoneal injection of a cocktail containing ketamine and xylazine (ketamine 100 mg, xylazine 20 mg/ml). The chest was opened and the heart quickly removed. The heart was briefly rinse in ice-cold Krebs-Henseleit solution (see below), and the aorta cannulated. The heart was then perfused at a flow rate of 10 ml/min with modified Krebs-Henseleit (K-H) solution containing NaCl 117.9, KCl 4.5, CaCl. 2.5, $MgSO_4$ 1.18, $KH_2PO_4$ 1.18, pyruvate 2.0 mmo/L. The K-H solution (pH 7.4) was gassed continuously with 95% $O_2$ and 5% $CO_2$ and warmed to 35±0.50° C. The heart was electrically paced at a fixed cycle length of 340 ms (250 beats/min) using a bipolar electrode place on the left atrium. The electrical stimuli were generated by a Grass stimulator (Model S48, W. Warwick, R.I.) and delivered through a Stimuli Isolation Unit (Model SIU5, Astro-Med, Inc., NY) as square-wave pulses of 3 msec in duration and amplitude of at least twice the threshold to intensity.

Coronary perfusion pressure (CPP) was measured using a pressure transducer, connected to the aortic cannula via a T-connector positioned approximately 3 cm above the heart. Coronary perfusion pressure was monitored throughout the experiment and recorded either on a chart recorder (Gould Recorder 2200S) or a computerized recording system (PowerLab/4S, ADInstruments Pty Ltd, Australia). Only hearts with CPP ranging from 60 to 85 mmHg (in the absence of drugs) were used in the study. Coronary conductance (in ml/min/mmHg) was calculated as the ratio between coronary perfusion rate (10 ml/min) and coronary perftision pressure.

Anesthetized open-chest pig preparation

Farm pigs weighing 22–27 kg were used in this study. All animals received humane care according to the guidelines set forth in "The Principles of Laboratory Animal Care" formulated by the National Society for Medical research and the "Guide for the Care and Use of Laboratory Animals" prepared by the Institute of Laboratory Animal Resources and published by the National Institutes of Health (NIH Publication No. 86-23, revised 1996). In addition, animals were used in accordance with the guidelines of the University of Kentucky Institutional Animal Care and Use Protocol.

Anesthesia was anesthetized with ketamine (20 mg/kg, i.m.) and sodium pentobarbital (15–18 mg/kg i.v.). Anesthesia was maintained with additional sodium pentobarbital (1.5–2 mg/kg, i.v.) every 15–20 minutes. Ventilation was maintained via a tracheotomy using a mixture of room air and 100% $O_2$. Tidal volume, respiratory rate and fraction of $O_2$ in inspired air were adjusted to maintain normal arterial blood gas (ABG) and pH values. Core body temperature was monitored with an esophageal temperature probe and maintained with a heating pad between 37.0–37.5° C. Lactate Ringers solution was administered via an ear or femoral vein, at 5–7 ml/kg/min after a initial bolus of 300–400 ml. A catheter was inserted into the femoral artery to monitor arterial blood pressure and to obtain ABG samples.

The heart was exposed through a median stemotomy, and suspended in a pericardial cradle. Left ventricular pressure (LVP) was measured with a 5 F high fidelity pressure sensitive tip transducer (Millar Instruments, Houston, Tex.) placed in the left ventricular cavity via the apex and secured with a purse string suture. A segment of the left anterior descending coronary artery (LAD), proximal to the origin of the first diagonal branch, was dissected free of, surrounding tissue. A transit time perivascular flow probe (Transonic Systems Inc., Ithaca, N.Y.) was placed around this segment to measure coronary blood flow (CBF). Proximal to the flow probe a 24 g modified angiocatheter was inserted for intracoronary infusions. All hemodynic data were continuously displayed on a computer monitor and fed through a 32 bit analog-digital converter into an online data acquisition computer with customized software (Augury, Coyote Bay Instruments, Manchester, N.H.). $A_{2A}$ AdoR agonists were dissolved in DMSO to produce stock concentrations of 1–5 mM, which were diluted in 0.9% saline and infused at rates of 1–1.5 ml/min. The $A_{2A}$ AdoR agonists were administered intracoronary. To maintain blood pressure constant, phenylephrine was administered intravenously. The phenylephrine stock solution (30 mM) was prepared in distilled water.

Isolated perfused hearts To determine the duration of the $A_{2A}$ adenosine receptor mediated coronary vasodilation caused by adenosine and adenosine receptor agonists, the agonists were administered interveneously by bolus injection. *Protocol: Bolus injections.* In each heart of this series (3 to 11 hearts for each agonist), boluses of adenosine (20 $\mu$l, $2\times10^{-4}$M), Compounds of this invention (20 to 40 $\mu$l, $2\times10^{-5}$ M), and other adenosine receptor agonists were injected into the perfusion line. The times to 50% (t 0.5) and 90% (t 0.9) reversal of the decrease in CPP were measured. Each heart was exposed to a maximum of three vasodilators. Relationship between affinity of various agonists for $A_{2A}$ adenosine receptor and the reversal time of their effect to increase coronary conductance: These experiments were performed to constrict the relationship between the affinities of the various agonists for $A_{2A}$ adenosine receptor and the duration of their respective effect on coronary conductance. Boluses of various agonists were injected into the perfusion line of rat isolated perfused hearts (n=4 to 6 for each agonist) and the time to 90% (t 0.9) reversal of the decrease in CPP measured. The affinities of the various agonists for $A_{2A}$ adenosine receptor was determined in pig striatum membranes using a radioligand binding assay, as described above. The reversal time (t 0.9) of the decrease in CPP was plotted against their affinities ($pK_i$) for the $A_{2A}$ adenosine receptor.

Open-chest pig

Prior to initiating the experiment, a 3-minute stabilization period followed the completion of all instrumentation. After obtaining the baseline hemodynamic data the first intracoronary infusion of an $A_{2A}$ ADOR agonist was initiated. Infusions were maintained for 4–5 minutes to allow LAD CBF to reach a steadystate, after which the infusion was terminated. The time to recovery of 50% (t 0.5) and 90% (t 0.9) of baseline CBF were recorded. Ten to 15 minutes after CBF returned to predrug values a second infusion with a different agonist was started. In preliminary studies it was found that the intracoronary infusion of adenosine agonists produced varying degrees of systemic hypotension, and hence, in all subsequent experiments, phenylephrine was administered intravenously. Hemodynamic measurements were made prior to and following the initiation of the phenylephrine infusion at dose of—1 μg/kg/min. The phenylephrine infusion rate was adjusted during and following the infusions of the adenosine agonists to maintain arterial blood pressure within 5 mmHg of preinfusion values. The effect of a maximum of three different agonists was determined in each experiment.

Results

Adenosine, the compounds of this invention and other adenosine derivatives were given as boluses into the perfusion line at concentrations that cause equal or near-equal increases in coronary conductance. Although adenosine and the agonists caused equal maximal increases in coronary conductance the duration of their effect was markedly different. The duration of the effect of adenosine was the shortest followed by Compound 18, Compound 12 and Compound 21, whereas that of CGS21680, YT-146, HENECA and WRC0470 were the longest. The durations of the coronary vasodilation caused by adenosine, the compounds of this invention and other agonists measured as the time to 50% and 90% (t 0.5 and t 0.9, respectively) reversal of the increases in coronary conductance are summarized in Table 4

TABLE 4

Reversal Time Of Coronary Vasodilation by Adenosine and adenosine receptor agonists in Rat Isolated Perfused Hearts

| Agonist | t 0.5 (min) | t 0.9 (min) | n |
|---|---|---|---|
| Adenosine | 1.06 ± 0.1 | 5.6 ± 0.8 | 11 |
| HENECA | 28.6 ± 1.1 | 32.8 ± 3.1 | 3 |
| R-PIA | 7.9 ± 0.1 | 12.6 ± 0.8 | 3 |
| CGS21680 | 14.5 ± 0.9 | 19.5 ± 0.9 | 3 |
| YT-146 | 17.7 ± 1.0 | 28.5 ± 4.0 | 3 |
| Compound 12 | 4.1 ± 0.3 | 9.8 ± 1.4 | 4 |
| Compound 18 | 3.4 ± 0.5 | 8.4 ± 2.2 | 4 |
| WRC-0470 | 21.9 ± 0.9 | 27.9 ± 1.4 | 6 |
| Compound 21 | 8.3 ± 0.4 | 12.6 ± 0.4 | 4 |

Time (in minutes) to 50% and 90% (t 0.5 and t 0.9, respectively) reversal of the increases in coronary conductance caused by adenosine and adenosine receptor agonists. Values are the means ± SEM of single determinations in each of the preparations (n).

The reversal time of coronary vasodilation was dependent on the affinity of the adenosine derivatives for brain striatum $A_{2A}$ receptors. There was a significant (P<0.05) inverse relationship (r=0.87) between the affinity ($PK_i$) of the agonists for the $A_{2A}$AdoR and the reversal time (t 0.9) of the coronary vasodilation caused by the same agonists.

Coronary Vasodilation in an Open-chest Pig Preparation

In in situ hearts of an open-chest anesthetized pig preparation Compounds 12 and 18 of this invention as well as CGS21680 and other $A_{2A}$AdoR agonists (i.e., WRC-0470 and YT-146) caused significant increases in coronary blood flow (CBF). Selected doses of these compounds given as continuous (4 to 5 min) intracoronary infusions caused 3.1 to 3.8-fold increases in CBF as set forth in Table 3, below. Once established that all agonists caused near the same magnitude of increases in CBF (i.e., "fold increase") and cause similar changes in heart rate and mean arterial blood pressure, the reversal time of their respective coronary vasodilation effects was determined.

TABLE 4

Magnitude of Increase in Coronary Blood Flow Caused by Various Adenosine Receptor Agonists in Open-Chest Anesthetized Pigs

| Agonist | CBF ("Fold Increase") | n |
|---|---|---|
| Compound 12 (30 μg/kg/min) | 3.78 ± 0.70 | 3 |
| Compound 18 (50 μg/kg/min) | 3.33 ± 0.58 | 3 |
| WRC-470 (1 μg/kg/min) | 3.14 ± 0.24 | 6 |
| GSC21680 (2 μg/kg/min) | 3.54 ± 0.093 | 3 |
| YT-146 (1 μg/kg/min) | 3.44 ± 0.47 | 3 |

Maximal "fold-increase" in coronary blood flow (CBF) above baseline caused by various adenosine receptor agonists. Data represent mean±SEM of one or two measurements in each pig (n).

As summarized in Table 5 the $t_{0.5}$ and $t_{0.9}$ of coronary vasodilation caused by the various $A_{2A}$ AdoR agonists and "CVT-compounds" was variable. The reversal time of the increase in CBF caused by Compounds 12 and 18 of this invention were shorter than that of CGS21680, WRC-0470 or YT-146. More importantly, as in rat isolated perfused hearts, there was a significant (P<0.05) inverse relationship (r=0.93) between the affinity ($PK_i$) of the $A_{2A}$AdoR agonists for pig brain striatum $A_{2A}$ receptors and the reversal time (t 0.9) of coronary vasodilation. There was an excellent concordance between the reversal time of the coronary vasodilation caused by a selected number of agonists in rat isolated perfused hearts and in anesthetized open chest pig preparations.

TABLE 5

Reversal Time of Coronary Vasodilation Caused by Various Adenosine Receptor Agonists in Open-Chest Anesthetized Pigs

| Agonist | $t_{0.5}$ (min) | $t_{0.9}$ (min) | n |
|---|---|---|---|
| Compound 12 (30 μg/kg/min) | 2.3 ± 0.6 | 9.6 ± 1.0 | 3 |
| Compound 18 (50 μg/kg/min) | 3.1 ± 0.9 | 12.0 ± 1.0 | 3 |
| WRC-470 (1 μg/kg/min) | 9.5 ± 0.8 | 22.5 ± 1.6 | 6 |
| GSC21680 (2 μg/kg/min) | 9.7 ± 0.8 | 21.4 ± 0.8 | 3 |
| YT-146 (1 μg/kg/min) | 17.8 ± 3.4 | 32.9 ± 5.6 | 3 |

Time (in minutes) to 50% and 90% ($t_{0.5}$ and $t_{0.9}$, respectively) reversal of the increases in coronary blood flow caused by adenosine receptor agonists. Values are the means ± SEM of one or two determinations in each animal (n).

Compound 18 is a low affinity $A_{2A}$AdoR agonists and less potent (−10-fold) than the prototypical agonist CGS21680. Nevertheless Compound 18 is a full agonists to cause coronary vasodilation. But, as shown in this study the duration of its effect is several-fold shorter than that of the high affinity agonists CGS21680 and WRC-0470. Hence, Compound 18 is a short acting $A_{2A}$ AdoR agonists coronary vasodilator. Because of their short duration of action in comparison to the high affinity $A_{2A}$AdoR agonists (e.g., WRC-0470, CGS21680) this low affinity but still full agonist coronary vasodilator may prove to be ideal pharmacological "stressor agents" during radionuclide imaging of the myocardium.

What we claim is:

1. A compound selected from the group consisting of:
(4S,2R,3R,5R)-2-{6-amino-2-[1-decylpyrazol-4-yl]purin-9-yl}-5-(hydroxymethyl)oxolane-3,4-diol, (4S,2R,3R,5R)-2-{6-amino-2-[1-(cyclohexylmethyl)pyrazol-4-yl]purin-9-yl}-5-(hydroxymethyl)oxolane-3,4-diol, (4S,2R,3R,5R)-2-{6-amino-2-[1-(2-phenylethyl)pyrazol-4-yl]purin-9-yl}-5-(hydroxymethyl)oxolane-3,4-diol, (4S,2R,3R,5R)-2-{6-amino-2-[1-(3-cyclohexylpropyl)pyrazol-4-yl]purin-9-yl}-5-(hydroxymethyl)oxolane-3,4-diol, and (4S,2R,3R,5R)-2-{6-amino-2-[1-(2-cyclohexylethyl) pyrazol-4-yl]purin-9-yl}-5-(hydroxymethyl)oxolane-3, 4-diol.

2. A method of stimulating coronary vasodilatation in a mammal by administering to the mammal a therapeutically effective amount of a compound of claim 1 that is sufficient to stress the heart and induce a coronary steal situation for the purposes of imaging the heart.

3. The method of claim 2 wherein the therapeutically effective amount ranges from about 0.01 to about 100 mg/kg weight of the mammal.

4. The method of claim 2 wherein the mammal is a human.

5. A pharmaceutical composition of matter comprising the compound of claim 1 and one or more pharmaceutical excipients.

6. The pharmaceutical composition of matter of claim 5 wherein the pharmaceutical composition is in the form of a solution.

* * * * *